United States Patent
Im et al.

(10) Patent No.: US 11,920,195 B2
(45) Date of Patent: Mar. 5, 2024

(54) METHOD FOR DIAGNOSING DRUG ADDICTION, METHOD FOR SCREENING THERAPEUTIC AGENT FOR DRUG ADDICTION AND PHARMACEUTICAL COMPOSITION FOR PREVENTING OR TREATING DRUG ADDICTION

(71) Applicant: KOREA INSTITUTE OF SCIENCE AND TECHNOLOGY, Seoul (KR)

(72) Inventors: Heh-In Im, Seoul (KR); Baek Sun Kim, Seoul (KR); Sung Hyun Tag, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 186 days.

(21) Appl. No.: 17/334,345

(22) Filed: May 28, 2021

(65) Prior Publication Data
US 2021/0403996 A1    Dec. 30, 2021

(30) Foreign Application Priority Data

Jun. 25, 2020  (KR) .................. 10-2020-0077727
Apr. 13, 2021  (KR) .................. 10-2021-0047804

(51) Int. Cl.
*C12Q 1/6876* (2018.01)
*C12Q 1/686* (2018.01)

(52) U.S. Cl.
CPC .......... *C12Q 1/6876* (2013.01); *C12Q 1/686* (2013.01); *C12Q 2600/178* (2013.01)

(58) Field of Classification Search
CPC .............. C12Q 1/6876; C12Q 1/686; C12Q 2600/178; C12Q 2600/136; C12Q 2600/158; C12Q 1/6883; A61K 45/00; A61P 25/30; G01N 33/6893; G01N 2800/307
See application file for complete search history.

(56) References Cited

FOREIGN PATENT DOCUMENTS

| KR | 10-2013-0084158 A | 7/2013 | |
| KR | 20190083110 | * 7/2019 | .......... C12Q 1/6883 |

OTHER PUBLICATIONS

NCBI Reference Sequence: NM_006372.4 "*Homo sapiens* synaptotagmin binding cytoplasmic RNA interacting protein (SYNCRIP), transcript variant 1, mRNA" PRI Feb. 21, 2019 Note: Seq ID No. 1 matches perfectly to nucleotides 440 to 3193 of NM_006372.4. (Year: 2019).*
KR20190083110 date: Jul. 2019 Inventor: Im Heh In Baek Sun Kim English Translation (Year: 2019).*
A dopamine-induced gene expression signature regulates neuronal function and cocaine response Katherine E. Savell, bioRxiv 781872; doi: https://doi.org/10.1101/781872 (Year: 2019).*
Federica Rizzo, SMN/SYNCRIP and RNA-Motif 7 in spinal muscular atrophy: RNA-Seq and motif analysis of human motor neurons, Brain, vol. 142, Issue 2, Feb. 2019, pp. 276-294, https://doi.org/10.1093/brain/awy330 (Year: 2019).*
Dana Most et al. "Synaptic microRNAs Coordinately Regulate Synaptic mRNAs: Perturbation by Chronic Alcohol Consumption". Publication Date: Aug. 5, 2015. Neuropsychopharmacology (2016) 41, 538-548.
Predicted: Theropithecus gelada synaptotagmin binding cytoplasmic RNA interacting protein (SYNCRIP), transcript variant X6, mRNA, National Library of Medicine, National Center for Biotechnology Information, Publication Date: Jun. 29, 2018.

* cited by examiner

*Primary Examiner* — Neil P Hammell
*Assistant Examiner* — Morgan T Lindgren Baltzell
(74) *Attorney, Agent, or Firm* — Rabin & Berdo, P.C.

(57) ABSTRACT

Disclosed is a composition for diagnosing, preventing or treating drug addiction based on synaptotagmin binding cytoplasmic RNA interacting protein (SYNCRIP). SYNCRIP or a gene encoding the protein can be used to diagnose drug addiction. In addition, a therapeutic agent for drug addiction can be discovered by measuring the expression of SYNCRIP. Furthermore, an agent expressing SYNCRIP or promoting the activity of SYNCRIP can be used to prevent or treat drug addiction.

7 Claims, 7 Drawing Sheets

Specification includes a Sequence Listing.

METHOD FOR DIAGNOSING DRUG ADDICTION, METHOD FOR SCREENING THERAPEUTIC AGENT FOR DRUG ADDICTION AND PHARMACEUTICAL COMPOSITION FOR PREVENTING OR TREATING DRUG ADDICTION

CROSS-REFERENCE TO RELATED APPLICATIONS

This application claims priority under 35 U.S.C. § 119 to Korean Patent Application Nos. 10-2020-0077727 and 10-2021-0047804 filed on Jun. 25, 2020 and Apr. 13, 2021 respectively in the Korean Intellectual Property Office, the disclosure of which is incorporated herein by reference in its entirety.

BACKGROUND OF THE INVENTION

1. Field of the Invention

The present invention relates to a method for diagnosing drug addiction, a method for screening a therapeutic agent for drug addiction, and a pharmaceutical composition for preventing or treating drug addiction.

2. Description of the Related Art

Drug addiction is a chronic brain disease or mental illness that leads to structural and functional changes in the brain, causing addicted people to compulsively seek and persistently use drugs despite negative and harmful consequences of the drugs. Most drug addicts use drugs voluntarily for the first time due to their curiosity or adventurous spirit but become dependent on drugs and have drug tolerance as time goes by. Drug tolerance is a phenomenon in which a higher dose of the drug is needed for the same effect whenever the drug is used. As a result of drug tolerance, when drug addicts stop taking drugs, withdrawal symptoms are likely to occur. These withdrawal symptoms cause abnormalities that are difficult to endure mentally as well as physically.

Similarly to other illnesses such as heart disease, drug addiction interferes with normal and healthy functions of tissues (organs) and causes very serious consequences. Drug addicts cannot live their normal life without using addictive drugs. For example, drug addicts show a tendency to pay more attention to certain things and suffer from symptoms such as paranoid schizophrenia, cardiac disorder, elevated blood pressure, vomiting, dyspnea, loss of sensory function, loss of consciousness, nightmares or confusion. When drug addicts are left standing for 6 to 12 hours after taking drugs, they suffer from withdrawal symptoms such as anxiety, insomnia, excessive sleepiness, and irritability that may cause even death.

As the number of drug users increases gradually in Korea, effective methods are needed to treat habitual drug users as well as prevent drug addiction.

Since drug addiction persists for a lifetime if left untreated, various efforts have been made at the national level to treat drug addiction. Nevertheless, since the exact mechanism of drug addiction has not been determined, effective therapeutics and therapies for drug addiction have not been developed.

Most of the currently developed therapeutic agents for drug addiction are dopaminergic agonists or antagonists. The dopaminergic agonists ameliorate narcolepsy or discomfort but act on only limited conditioned stimuli, increasing the risk of recurrence. Another risk of the therapeutic agents is their addictiveness. On the other hand, dopaminergic receptor antagonists reduce the response to conditioned stimuli and are less likely to compensate for drugs but increase the risk that they may cause side effects associated with the dopaminergic nervous system, such as dullness of emotion, discomfort, and tardive dyskinesia (e.g., Parkinson's disease.).

In attempts to solve the above-mentioned problems, studies have been made to develop therapeutic agents for drug addiction from naturally occurring substances. For example, bergenin derivatives have been developed that have a good inhibitory activity on drug addiction, are very safe, and cause no fatal side effects (see Korean Patent Publication No. 10-2013-0084158). However, the bergenin derivatives are not substantially used for the treatment of drug addiction due to their insufficient therapeutic effects on drug addiction.

Attempts have been made to develop various diagnostic or therapeutic agents for drug addiction but there are still limitations and problems such as side effects. Thus, there is an urgent need to develop safe and effective therapeutic agents for drug addiction.

SUMMARY OF THE INVENTION

The present invention has been made in an effort to solve the above-described problems and one object of the present invention is to provide a biomarker composition for diagnosing drug addiction and a kit for diagnosing drug addiction.

A further object of the present invention is to provide a method for providing information necessary for the diagnosis of drug addiction.

Another object of the present invention is to provide a method and composition for screening a candidate agent capable of preventing or treating drug addiction.

Still another object of the present invention is to provide a pharmaceutical composition for preventing or treating drug addiction.

One aspect of the present invention provides a biomarker composition for diagnosing drug addiction including, as an active ingredient, synaptotagmin binding cytoplasmic RNA interacting protein (SYNCRIP) or a gene encoding the protein.

A further aspect of the present invention provides a composition for diagnosing drug addiction including, as an active ingredient, an agent for measuring the expression level of synaptotagmin binding cytoplasmic RNA interacting protein (SYNCRIP).

The agent for measuring the expression level of SYNCRIP may be selected from the group consisting of: primers and probes that specifically bind to the SYNCRIP gene; and antibodies, peptides, aptamers, and compounds that specifically bind to the SYNCRIP.

The SYNCRIP gene may have the sequence set forth in SEQ ID NO: 1.

Another aspect of the present invention provides a kit for diagnosing drug addiction including the composition.

Another aspect of the present invention provides a method for providing information necessary for the diagnosis of drug addiction, including (1) separating a biological sample from a subject and measuring the expression level of synaptotagmin binding cytoplasmic RNA interacting protein (SYNCRIP) or the mRNA expression level of the SYNCRIP gene in the biological sample, (2) comparing the expression level of SYNCRIP or the mRNA expression level of the SYNCRIP gene with that in a normal control sample, and (3)

diagnosing the subject as having drug addiction if the expression level of SYNCRIP or the mRNA expression level of the SYNCRIP gene is lower than that in the normal control sample.

The method may further include measuring the expression level of miR-137 in the biological sample from the subject.

Another aspect of the present invention provides a method for screening a therapeutic agent for drug addiction, including a) inducing drug addiction in an animal and treating the drug-addicted animal or a sample separated therefrom with a candidate agent, b) measuring the expression level of the SYNCRIP gene in the candidate agent-treated group, and c) selecting the candidate agent as a therapeutic agent for drug addiction if the measured expression level of the SYNCRIP gene is higher than that in a control group untreated with the candidate agent.

The SYNCRIP gene may have the sequence set forth in SEQ ID NO: 1.

The expression levels may be measured using a technique selected from the group consisting of polymerase chain reaction (PCR), quantitative polymerase chain reaction (qPCR), reverse transcription polymerase chain reaction (RT-PCR), competitive reverse transcription polymerase chain reaction (competitive RT-PCR), quantitative real-time polymerase chain reaction (qRT-PCR), real-time reverse transcription polymerase chain reaction (real-time RT-PCR), RNase protection assay, Northern blot analysis, and DNA chip analysis.

The method may further include measuring the expression level of miR-137 in the serum of the candidate agent-treated group.

The method may further include determining the candidate agent as a therapeutic agent for drug addiction if the measured expression level of miR-137 is higher than that in the control group untreated with the candidate agent.

Yet another aspect of the present invention provides a pharmaceutical composition for preventing or treating drug addiction, including, as an active ingredient, an agent expressing synaptotagmin binding cytoplasmic RNA interacting protein (SYNCRIP) or promoting the activity of SYNCRIP.

The agent expressing SYNCRIP or promoting the activity of SYNCRIP may be a vector containing the SYNCRIP gene.

The vector may be selected from the group consisting of linear DNAs, plasmid DNAs, recombinant non-viral vectors, recombinant viral vectors, and inducible gene expression vector systems.

The biomarker composition of the present invention, which includes, as an active ingredient, synaptotagmin binding cytoplasmic RNA interacting protein (SYNCRIP) or a gene encoding the protein, is effective in diagnosing drug addiction or detecting whether drugs are taken. It has been found that the expression of SYNCRIP in the brain striatum of a drug addiction animal model is reduced. It has also been found that when the expression of SYNCRIP in the brain striatum of a drug addiction animal model is increased, the expression of serum miR-137, a biomarker for drug addiction, is restored to a normal level. These findings demonstrate the availability of the biomarker composition for the diagnosis of drug addiction.

In addition, it has been found experimentally that an increase in the expression level of SYNCRIP inhibits a reduction in the expression of miR-137 in the serum of a drug addiction animal model. Based on this finding, a therapeutic agent for drug addiction can be discovered by measuring the expression of SYNCRIP. The therapeutic agent is expected to be useful in fields related to the development of pharmaceuticals, foods, etc.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
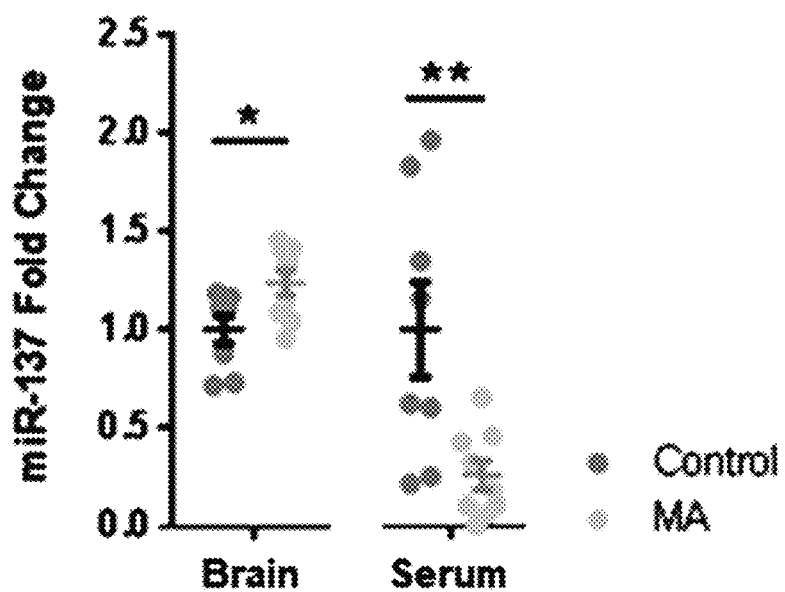
FIG. 1 compares the expression levels of miR137 in serum and brain striatum samples from a control group and a drug addiction animal model (MA)

Several aspects and various embodiments of the present invention will now be described in more detail.

The present inventors have earnestly conducted research to obtain a method for finding an agent capable of diagnosing drug addiction, and as a result, succeeded in identifying SYNCRIP interacting with miR-137, a biomarker for drug addiction. Based on this, the present invention has been accomplished.

One aspect of the present invention is directed to a biomarker composition for diagnosing drug addiction including, as an active ingredient, synaptotagmin binding cytoplasmic RNA interacting protein (SYNCRIP) or a gene encoding the protein.

The biomarker composition may further include a biomarker for drug addiction previously known in the art. The known biomarker may be, for example, miR-137, but is not particularly limited thereto.

As used herein, the term "synaptotagmin binding cytoplasmic RNA interacting protein (SYNCRIP)" refers to a gene that encodes a member of the cellular heterogeneous nuclear ribonucleoprotein (hnRNP) family. hnRNP is an RNA-binding protein that forms a complex with heterogeneous nuclear RNA (hnRNA) and regulates alternative splicing, polyadenylation, and other aspects of mRNA metabolism and transport. The encoded protein plays a variety of roles in mRNA growth and is associated with apoB RNA editing complexes and multiprotein complexes containing the survival of and motor neurons (SMNs). Many variants associated with the SYNCRIP gene have been observed to date, and their pseudogenes are known to be located in the short sequence of chromosome 20.

The SYNCRIP may have the sequence set forth in SEQ ID NO: 1 that is registered in the National Center for Biotechnology Information (NCBI) database under Gene ID: 10492. The SYNCRIP may include a sequence having a homology of at least 70%, preferably at least 80%, more preferably at least 90%, most preferably at least 95% to the sequence as forth in SEQ ID NO: 1.

As used herein, the term "drug addiction" is a substance-induced disorder and refers collectively to symptoms that are caused when a highly addictive drug is administered or taken. Drug addiction is considered a type of drug dependence and can be defined as a state in which a person has lost the power of self-control to continuously seek or take drugs despite an emotional state such as physical or mental impairment. That is, drug addiction can also be defined as long-term exposure to drugs.

Drug addiction is a disease caused by the use of illegal drugs such as heroin or legal drugs such as tranquilizers without medical supervision. Drug addiction may cause psychological and physical problems as well as interpersonal problems. In the present invention, drug addiction is intended to include drug misuse, drug abuse, drug dependence, and substance withdrawal.

The drug is not particularly limited as long as it is classified as a narcotic in the art. The drug is preferably selected from the group consisting of methamphetamine, amphetamine, cocaine, ecstasy, methylphenidate, and combinations thereof. The drug is more preferably methamphetamine.

Drug abuse is diagnosed when one or more of the following four cases last for one year or more to cause clinically significant disorders or afflictions: (1) the case where drug use prevents the user from performing his/her own important duties at work, school or home (for example, frequent absences, low school performance, disciplinary actions such as suspension or expulsion or family discord); (2) the case where drug use is continued even when the user knows that he/she is in a physically dangerous situation (for example, driving a car, riding a bicycle or motorcycle or handling machinery after drug use); (3) the case where drug use causes legal problems (for example, the user is arrested for criminal actions related to drug use); and (4) the case where drug use is continued despite persistent and repetitive social or interpersonal problems caused or aggravated by drug use (for example, family discord or violence).

As used herein, the term "drug dependence" refers collectively to addiction to highly addictive drugs when administered or taken and is also called drug addiction. More specifically, drug dependence can be defined as a state in which a person has lost the power of self-control to continuously seek or take drugs despite an emotional state such as physical or mental impairment. That is, drug dependence can also be defined as long-term exposure to drugs. Specifically, drug dependence is diagnosed when three or more of the following six cases last for one year or more to cause clinically significant disorders or afflictions: (1) the case where the amount of drugs used increases gradually or the effect of drugs decreases gradually despite the same amount of the drugs; (2) the case where withdrawal symptoms such as hand tremor, excessive sweating, rapid pulse, insomnia, nausea, vomiting, hallucination, anxiety, nervousness or epilepsy are caused when drug use is stopped or reduced, or the same amount of drugs as before is used to eliminate withdrawal symptoms; (3) the case where a larger amount of drugs is used for a longer time than expected once drug use has begun; (4) the case where an attempt to stop drug use is failed; (5) the case where drug use interrupts or prevents many important interpersonal relationships or professional activities; and (6) the case where drug use is continued even when the user knows that he/she has a psychological or physical disease (e.g., depression or liver disease) caused by drug use.

As used herein, the term "substance withdrawal" means that a craving to take highly addictive drugs is induced during the withdrawal period without taking the drugs in a state in which the dependence on the drugs is high by repeated administration of the drugs and refers collectively to symptoms of various mental disorders caused thereby.

As used herein, the term "diagnosis" is intended to include determining the susceptibility of an object to a particular disease or disorder, determining whether an object currently has a particular disease or disorder, determining the prognosis of an object with a particular disease or disorder, or therametrics (e.g., monitoring the condition of the object to provide information on treatment efficacy).

The relationship between SYNCRIP and drug addiction is not yet known. In the Examples section that follows, however, the expression of the SYNCRIP gene in a drug addiction animal model was found to be significantly low compared to that in a control group.

In the Examples section that follows, when SYNCRIP was overexpressed in a drug addiction animal model, the expression of the miR-137 gene, a biomarker for drug addiction, in serum was restored to a normal level. This indicates that SYNCRIP correlates with drug addiction, suggesting that SYNCRIP can be utilized as a biomarker capable of diagnosing drug addiction. The expression level of SYNCRIP or a gene encoding the protein can be measured to detect whether drug addiction is diagnosed.

As used herein, the term "expression" refers to the production of a protein or nucleic acid in a cell. The term "protein" is used interchangeably with "polypeptide" or "peptide" and, for example, refers to a polymer of amino acid residues, as commonly found in naturally occurring proteins. The term "polynucleotide" or "nucleic acid" refers to deoxyribonucleotide (DNA) or ribonucleotide (RNA) in either single- or double-stranded form. Unless otherwise limited, the term encompasses known analogs of natural nucleotides that hybridize to nucleic acids in a manner similar to naturally occurring nucleotides. The term "mRNA" refers to an RNA that transfers genetic information (gene-specific nucleotide sequence) to ribosomes that specify amino acid sequences from a specific gene during protein synthesis.

A further aspect of the present invention is directed to a composition for diagnosing drug addiction including, as an active ingredient, an agent for measuring the expression level of synaptotagmin binding cytoplasmic RNA interacting protein (SYNCRIP).

The agent for measuring the expression level of SYNCRIP may be selected from the group consisting of: primers and probes that specifically bind to the SYNCRIP gene; and antibodies, peptides, aptamers, and compounds that specifically bind to the SYNCRIP.

As used herein, the term "primer" refers to a short nucleic acid sequence that has a free 3'-hydroxyl group, can form a base pair with a complementary template, and serves as a starting point for replicating the template strand. The primer can initiate DNA synthesis in the presence of a reagent for polymerization (e.g., DNA polymerase or reverse transcriptase) and four different nucleoside triphosphates in a suitable buffer at a proper temperature. PCR conditions and the lengths of the sense and antisense primers can be appropriately selected according to techniques known in the art.

As used herein, the term "probe" refers to a fragment of a nucleic acid such as RNA or DNA corresponding to several to hundreds of bases that can bind specifically to mRNA and can be labeled to determine the presence and expression level of specific mRNA. The probe can be constructed in the form of an oligonucleotide probe, a single-stranded DNA probe, a double-stranded DNA probe, an RNA probe, etc. Suitable probes and hybridization conditions can be selected according to techniques known in the art.

The primer or probe can be chemically synthesized using a phosphoramidite solid support method or other widely known methods. The primer or probe may be modified in various ways by methods known in the art as long as it does not interfere with its hybridization with SYNCRIP mRNA. Examples of such modifications include methylation, capping, substitution of native nucleotides with one or more homologues, and inter-nucleotide modifications such as binding of labeling materials using uncharged (e.g., methyl phosphonate, phosphotriester, phosphoramidate, and carbamate) or charged linkers (e.g., phosphorothioate and phosphorodithioate) and fluorescence or enzymes.

The agent for measuring the expression level of SYNCRIP may be an antibody, peptide, aptamer or compound that specifically binds to SYNCRIP.

As used herein, the term "antibody" is a term known in the art and refers to a specific immunoglobulin that is directed against an antigenic site. The antibody means an antibody that binds specifically to SYNCRIP. The antibody can be produced by a suitable method known in the art. The antibody is intended to include polyclonal antibodies, monoclonal antibodies, and all immunoglobulin antibodies. The antibody means a complete form with two full-length light chains and two full-length heavy chains. The antibody is also intended to include special antibodies such as humanized antibodies.

As used herein, the term "aptamer" refers to a single-stranded nucleic acid (DNA, RNA, or modified nucleic acid) having a stable tertiary structure. The aptamer is a substance capable of binding specifically to an analyte to be detected in a sample. The aptamer specifically determines the presence of a target protein in a sample. The aptamer can be produced in accordance with a suitable method known in the art by sequencing and synthesizing an oligonucleotide having high selectivity and binding ability to a target protein (SYNCRIP in the present invention) and modifying the 5' or 3' end of the oligonucleotide with —SH, —COOH, —OH or $NH_2$ for binding to a functional group of an aptamer chip, but the production of the aptamer is not limited to this method.

The diagnostic composition of the present invention may further include an agent necessary for a known method for detecting a protein, in addition to the SYNCRIP-specific antibody. The known method can be used in combination with the diagnostic composition without limitation to measure the expression level of SYNCRIP in a subject.

Since the nucleic acid sequence of the gene is registered in the Gene Bank, those skilled in the art can design an antisense oligonucleotide, a primer pair or a probe that specifically amplify a specific region of the gene based on the sequence.

The antisense oligonucleotide, the primers or the probe can be chemically synthesized using a phosphoramidite solid support method or other widely known methods. The nucleic acid sequence may be modified by many means known in the art. Non-limiting examples of such modifications include methylation, capping, substitution of native nucleotides with one or more homologues, and inter-nucleotide modifications such as modifications with uncharged (e.g., methyl phosphonate, phosphotriester, phosphoramidate, and carbamate) or charged linkers (e.g., phosphorothioate and phosphorodithioate).

Another aspect of the present invention is directed to a kit for diagnosing drug addiction including an agent for measuring the expression level of synaptotagmin binding cytoplasmic RNA interacting protein (SYNCRIP).

The diagnostic kit of the present invention may include one or more other compositions, solutions or devices suitable for assay as well as antibodies recognizing SYNCRIP as a marker and primers and probes recognizing SYNCRIP mRNA as a marker.

In one embodiment, the kit may include essential elements necessary to perform a reverse transcription polymerase chain reaction (RT-PCR). The RT-PCR kit includes a pair of primers specific to each marker gene. The primer is a nucleotide having a sequence specific to the nucleic acid sequence of each marker gene and is about 7 bp to 50 bp in length, more preferably about 10 bp to 30 bp in length. The kit may also include a primer specific to the nucleic acid sequence of a control gene. The RT-PCR kit may further include a test tube or a suitable container, a reaction buffer (whose pH and magnesium concentration vary), deoxynucleotides (dNTPs), enzymes such as Taq-polymerase and reverse transcriptase, DNAse, RNAse inhibitor DEPC-water, and sterilized water.

In another embodiment, the diagnostic kit may include essential elements necessary to operate a DNA chip. The DNA chip kit may include a substrate to which a cDNA or oligonucleotide corresponding to a gene or its fragment is attached and reagents, agents, and enzymes for constructing fluorescently labeled probes. The substrate may include a cDNA or oligonucleotide corresponding to a control gene or its fragment.

The sample used for analysis is a biological sample in which a cancer-specific protein associated with a drug-addicted state distinguishable from a healthy state can be identified. Examples of suitable biological samples include blood, hemocytes, brain tissues, neurons, cerebrospinal fluid, saliva, nasal fluid, sputum, synovial fluid, amniotic fluid, ascites, cervical and vaginal secretions, and urine. The biological sample is preferably selected from the group consisting of blood, hemocytes, brain tissues, neurons, and cerebrospinal fluid. The sample may be prepared such that the detection sensitivity to the protein marker is enhanced. For example, a serum sample from a patient may be pretreated by anion exchange chromatography, affinity chromatography, size exclusion chromatography, liquid chromatography, sequential extraction or gel electrophoresis.

Another aspect of the present invention is directed to a method for providing information necessary for the diagnosis of drug addiction, including (1) separating a biological sample from a subject and measuring the expression level of synaptotagmin binding cytoplasmic RNA interacting protein (SYNCRIP) or the mRNA expression level of the SYNCRIP gene in the biological sample, (2) comparing the expression level of SYNCRIP or the mRNA expression level of the SYNCRIP gene with that in a normal control sample, and (3) diagnosing the subject as having drug addiction if the expression level of SYNCRIP or the mRNA expression level of the SYNCRIP gene is lower than that in the normal control sample.

First, (1) a biological sample is separated from a subject and the expression level of synaptotagmin binding cytoplasmic RNA interacting protein (SYNCRIP) or the mRNA expression level of the SYNCRIP gene in the biological sample is measured.

As used herein, the term "subject" refers to any single individual who is suspected of drug addiction and requires a diagnosis of drug addiction. The subject is intended to include humans, cows, dogs, guinea pigs, rabbits, chickens, insects, mice, and rats. Any subject who participated in a clinical or epidemiological study and had no clinical finding of drug addiction disease may be used as a control. In one embodiment of the present invention, a mouse or rat is used as the subject.

As used herein, the term "subject who is suspected of drug addiction" refers to a subject who seems to have withdrawal symptoms due to misuse or abuse of addictive drugs, addiction to drugs or long-term drug abuse.

The biological sample can be used without limitation as long as it is collected from a subject whose drug addiction is to be diagnosed. For example, the biological sample may be selected from the group consisting of blood, hemocytes, brain tissues, neurons, cerebrospinal fluid, saliva, nasal fluid, sputum, synovial fluid, amniotic fluid, ascites, cervical and vaginal secretions, and urine. The biological sample is preferably selected from the group consisting of blood, hemocytes, brain tissues, neurons, and cerebrospinal fluid but is not especially limited thereto.

As used herein, the term "measurement" preferably means "analysis", specifically "qualitative analysis" for measuring and determining the presence of a target material or "quantitative analysis" for measuring and determining the level of presence (expression level) of a target material or the change in the amount of a target material. The measurement may be performed by both qualitative and quantitative methods. Preferably, the measurement is performed quantitatively.

The sample may be pretreated before use for detection or diagnosis. Examples of suitable pretreatment techniques include homogenization, filtration, distillation, extraction, concentration, inactivation of interfering components, and addition of reagents.

The expression level of the protein can be measured by suitable methods known in the art, including, but not limited to, Western blotting, ELISA, radioimmunoassay, radioimmunodiffusion, Ouchterlony immunodiffusion, rocket immunoelectrophoresis, immunohistostaining, immunoprecipitation assay, complement fixation assay, FACS, and protein chip analysis.

The expression level of the gene can be measured by suitable methods known in the art, including, but not limited to, polymerase chain reaction (PCR), quantitative polymerase chain reaction (qPCR), reverse transcription polymerase chain reaction (RT-PCR), competitive reverse transcription polymerase chain reaction (competitive RT-PCR), quantitative real-time polymerase chain reaction (qRT-PCR), real-time reverse transcription polymerase chain reaction (real-time RT-PCR), RNase protection assay, Northern blot analysis, and DNA chip analysis. More preferably, the expression level of the gene is measured by quantitative polymerase chain reaction (qPCR) or Northern blot analysis.

Next, the expression level of SYNCRIP or the mRNA expression level of the SYNCRIP gene in the subject sample is compared with that in a normal control sample, which is measured by the same method (step (2)). Preferably, the subject and normal control samples are obtained from the same species by the same method.

Finally, the subject is diagnosed as having drug addiction if the expression level of SYNCRIP or the mRNA expression level of the SYNCRIP gene is lower than that in the normal control sample (step (3)). Specifically, the subject is diagnosed as having drug addiction if the measured expression level of SYNCRIP in the subject sample is lower than that in the sample from the healthy control group.

That is, according to the method of the present invention, the expression level of a biomarker (SYMCRIP) in a biological sample from a subject who is suspected of drug addiction is measured and compared with the expression level of the biomarker (SYMCRIP) in a biological sample from a normal control group of the same species as the subject, in which the two samples are obtained by the same method, and the subject is diagnosed as having drug addiction if the expression level of the biomarker in the subject sample is lower than that in the normal control sample.

Another aspect of the present invention is directed to a method for screening a therapeutic agent for drug addiction, including a) inducing drug addiction in an animal and treating the drug-addicted animal or a sample separated therefrom with a candidate agent, b) measuring the expression level of the SYNCRIP gene in the candidate agent-treated group, and c) selecting the candidate agent as a therapeutic agent for drug addiction if the measured expression level of the SYNCRIP gene is higher than that in a control group untreated with the candidate agent.

As used herein, the term "drug-addicted animal" refers to an animal in which drug addiction is induced by long-term drug administration. The animal may be a mammal other than a human being, preferably a mouse, a guinea pig, a pig or a bird.

As used herein, the term "separated sample" refers to a tissue or cell sample separated from the drug-addicted animal. The sample is intended to include tissues or cells of the drug-addicted animal in which the expression level of the SYNCRIP gene can be detected. The sample is preferably a tissue or cell sample separated from the brain of the drug-addicted animal but is not limited thereto.

As used herein, the term "candidate agent" refers to a substance to be tested for therapeutic activity against drug addiction and is intended to include extracts, proteins, oligopeptides, small organic molecules, polysaccharides, polynucleotides, and molecules of a wide range of compounds. The "candidate agent" may be a cell transfected with a liposome or vector. The transfection may be performed by microinjection, calcium phosphate co-precipitation, electroporation or liposome fusion but is not limited thereto.

As used herein, the term "group untreated with the candidate agent" refers to a drug-addicted animal without treatment with the candidate agent or a sample separated from the drug-addicted animal. The group untreated with the candidate agent is in a parallel relationship with the group treated with the candidate agent. The group untreated with the candidate agent is also referred to as a control group.

In the present invention, the screening can be performed by comparing the expression of SYNCRIP capable of upregulating miR-137, a biomarker for drug addiction, present in the serum of the group treated with the candidate agent with that in the control group untreated with the candidate agent.

In the present invention, drug addiction in animals is induced with methamphetamine as an addictive drug. That is, the drug addiction is specifically induced by an addictive drug. Any addictive drug that is classified as a narcotic or addictive drug in the art may be used without particular limitation. The addictive drug is preferably selected from the group consisting of methamphetamine, amphetamine, cocaine, ecstasy, methylphenidate, and mixtures thereof.

In the Examples section that follows, the expression level of miR-137 in a brain tissue of a drug addiction animal model was found to be significantly higher than that of a normal animal model, whereas the expression of miR-137 in the serum of the drug addiction animal model was found to be significantly lower than that of the normal animal model. These results again demonstrate that the miR-137 gene acts as a biomarker for drug addiction, which is described in the literature.

Analysis revealed that the overexpression of SYNCRIP normalizes the expression level of miR-137 in the serum of a drug addiction model induced by methamphetamine administration compared to that of a control group. That is, drug addiction symptoms due to the administration of the drug and the reduced expression level of miR-137 in the serum caused by the drug addiction symptoms are remarkably inhibited in a SYNCRIP overexpressing animal model, indicating that SYNCRIP is useful as a target for preventing or treating drug addiction caused by long-term drug administration and its withdrawal symptoms.

It has also been found that SYNCRIP can induce the behavior (egocentric spatial learning behavior) of animal models with withdrawal symptoms caused by drug addiction to a normal level and has an inhibitory effect on increased activity induced by administration of drugs to drug-addicted animal models after the withdrawal period.

As used herein, the term "prevention" or "preventing" means all actions that inhibit or delay the development of the drug addiction and its symptoms. As used herein, the term "treatment" or "treating" means all actions that alleviate or beneficially change drug addiction symptoms and withdrawal symptoms due to drug addiction.

In the method of the present invention, b) the expression level of the SYNCRIP gene in the candidate agent-treated group is measured and c) the candidate agent is selected as a therapeutic agent for drug addiction if the measured expression level of the SYNCRIP gene is higher than that in a control group untreated with the candidate agent.

Specifically, the expression level of the SYNCRIP gene in the drug-addicted animal or a sample separated therefrom is measured in the absence of the candidate agent for preventing or treating drug addiction (a group untreated with the candidate agent), the expression level of the SYNCRIP gene is measured in the presence of the candidate agent, the two expression levels are compared, and the candidate agent is estimated or judged as a substance for preventing or treating drug addiction when the measured expression level of the SYNCRIP gene in the presence of the candidate agent is higher than that in the absence of the candidate agent.

As used herein, the term "measurement of the gene expression level" means that the expression levels of the SYNCRIP gene in the drug-addicted animals or samples separated therefrom are measured in the absence and presence of the candidate agent to determine the amounts of mRNA.

The expression level of the gene can be measured using a technique selected from the group consisting of polymerase chain reaction (PCR), quantitative polymerase chain reaction (qPCR), reverse transcription polymerase chain reaction (RT-PCR), competitive reverse transcription polymerase chain reaction (competitive RT-PCR), quantitative real-time polymerase chain reaction (qRT-PCR), real-time reverse transcription polymerase chain reaction (real-time RT-PCR), RNase protection assay, Northern blot analysis, and DNA chip analysis. Quantitative polymerase chain reaction (qPCR) or Northern blot analysis.

The method of the present invention may further include measuring the expression level of miR-137 in the serum of the candidate agent-treated group. The method may further include determining the candidate agent as a therapeutic agent for drug addiction if the measured expression level of miR-137 is higher than that in the control group untreated with the candidate agent.

miR-137 is an agent that can be used to distinguish and diagnose whether drug addiction or its withdrawal symptoms occur. miR-137 is widely known as a biomarker for the diagnosis of drug addiction or withdrawal symptoms. Specifically, when drug addiction or withdrawal symptoms due to drug addiction occurs, the expression level of miR-137 relatively increases in the brain tissue and relatively decreases in the serum.

Although the relationship between the SYNCRIP gene and drug addiction and the relationship between SYNCRIP and miR-137 are not yet known, the present invention revealed that drug addiction reduces the expression of the SYNCRIP gene. In addition, overexpression of SYNCRIP in an animal was found to significantly increase the expression of the miR-137 gene, a biomarker for drug addiction, in serum. These results indicate that the SYNCRIP gene can function as a marker for screening a therapeutic agent for drug addiction.

The treatment with the candidate agent screened by the method of the present invention can promote or increase the expression level of the SYNCRIP gene compared to the untreatment control.

Another aspect of the present invention is directed to a composition or kit for screening a therapeutic agent for drug addiction, including, as an active ingredient, an agent for measuring the expression level of synaptotagmin binding cytoplasmic RNA interacting protein (SYNCRIP).

Although the relationship between the SYNCRIP gene and drug addiction and the relationship between SYNCRIP and miR-137 are not yet known, the present invention revealed that drug addiction reduces the expression of the SYNCRIP gene. In addition, overexpression of SYNCRIP in an animal was found to significantly increase the expression of the miR-137 gene, a biomarker for drug addiction, in serum. These results indicate that the SYNCRIP gene can function as a marker for screening a therapeutic agent for drug addiction. That is, any agent for measuring the expression level of the SYNCRIP gene may be used to screen a prophylactic or therapeutic agent for drug addiction.

The agent for measuring the expression level can be selected from the group consisting of primers, probes, and antibodies that bind specifically to the SYNCRIP gene.

As used herein, the term "primer" refers to a short nucleic acid sequence that has a free 3'-hydroxyl group, can form a base pair with a complementary template, and serves as a starting point for replicating the template strand. The primer can initiate DNA synthesis in the presence of a reagent for polymerization (e.g., DNA polymerase or reverse transcriptase) and four different nucleoside triphosphates in a suitable buffer at a proper temperature. PCR conditions and the lengths of the sense and antisense primers can be appropriately selected according to techniques known in the art.

As used herein, the term "probe" refers to a fragment of a nucleic acid such as RNA or DNA corresponding to several to hundreds of bases that can bind specifically to mRNA and can be labeled to determine the presence and expression level of specific mRNA. The probe can be constructed in the form of an oligonucleotide probe, a single-stranded DNA probe, a double-stranded DNA probe, an RNA probe, etc. Suitable probes and hybridization conditions can be selected according to techniques known in the art.

As used herein, the term "antibody" is a term known in the art and refers to a specific immunoglobulin that is directed against an antigenic site. The antibody means an antibody that binds specifically to SYNCRIP. The antibody can be produced by a suitable method known in the art. The antibody is intended to include polyclonal antibodies, monoclonal antibodies, and all immunoglobulin antibodies. The antibody means a complete form with two full-length light chains and two full-length heavy chains. The antibody is also intended to include special antibodies such as humanized antibodies.

Yet another aspect of the present invention is directed to a pharmaceutical composition for preventing or treating drug addiction, including, as an active ingredient, an agent expressing synaptotagmin binding cytoplasmic RNA interacting protein (SYNCRIP) or promoting the activity of SYNCRIP.

The relationship between the SYNCRIP gene and drug addiction symptoms is not yet known. In the Examples section that follows, however, drug addiction was found to reduce the expression of the SYNCRIP gene. Overexpression of SYNCRIP in an animal was also found to restore the expression of miR-137, a biomarker for drug addiction, to a normal level. Overexpression of SYNCRIP in a drug addiction animal model was also found to suppress withdrawal symptoms due to drug addiction, including spatial learning disorder and drug-induced hyperactivity. These findings indicate that any agent expressing the SYNCRIP gene or promoting the activity of the SYNCRIP gene may function to prevent or treat drug addiction.

The agent expressing SYNCRIP or promoting the activity of SYNCRIP is intended to include substances that promote the translation of SYNCRIP mRNA, but is not particularly limited thereto.

In one embodiment of the present invention, the agent expressing SYNCRIP or promoting the activity of SYNCRIP may be a vector containing the SYNCRIP gene or a therapeutic agent for drug addiction screened by the screening method described above.

The vector refers to a means for expressing a target gene in a host cell. The vector includes elements for the expression of a target gene. For example, the vector may include a replication origin, a promoter, an operator, and a transcription terminator. The vector may optionally further include an appropriate enzyme site (e.g., a restriction enzyme site) for introduction into the genome of a host cell, and/or a selectable marker for identifying successful introduction into the host cell, and/or a ribosome binding site (RBS) or internal ribosome entry site (IRES) for translation into a protein. The vector may further include a transcriptional regulatory sequence (e.g., an enhancer) other than the promoter.

The vector may be a plasmid DNA, a recombinant vector or any other mediator known in the art. Specifically, the vector may be a linear DNA, a plasmid DNA, a recombinant non-viral vector, a recombinant viral vector or an inducible gene expression vector system. The recombinant viral vector may be a retrovirus, adenovirus, adeno associated virus, helper-dependent adenovirus, herpes simplex virus, lentivirus or vaccinia virus vector but is not limited thereto.

The vector means an expression vector for gene therapy. As used herein, the term "gene therapy" refers to a method for treating various genetic diseases caused by genetic abnormality by inserting a normal gene into genetically abnormal cells or providing a new function to genetically abnormal cells to normalize the functions of the cells. That is, the expression vector for gene therapy means an expression vector that delivers the SYNCRIP gene to normal cells in the body to express the gene so that a new function is provided through cell fusion between genetically abnormal cells and the normal cells to normalize the functions of the cells.

A primer capable of specifically recognizing the SYNCRIP gene is constructed from the known sequence, the gene is amplified by polymerase chain reaction using the primer, the amplified gene is introduced into the expression vector, and the expression vector containing the amplified gene is introduced into cells. Exemplary methods for introduction of the expression vector include, but are not limited to, liposome-mediated transfection, calcium phosphate precipitation, DEAE-dextran-mediated transfer, positively charged lipid-mediated transfection, electroporation, transduction using phage systems, and viral infection.

According to one embodiment of the present invention, the composition may include 0.00001 to 30% by weight of the agent expressing SYNCRIP or promoting the activity of SYNCRIP, based on its total weight.

According to the embodiments described above, when the expression or activity of SYNCRIP is promoted, the expression of miR-137 associated with drug addiction can be regulated to prevent or treat drug addiction or withdrawal symptoms due to drug addiction.

The pharmaceutical composition can be used to prevent or treat drug addiction. The pharmaceutical composition can be presented into formulations suitable for topical application. For example, the pharmaceutical composition may be administered via a route selected from the group consisting of oral administration, transdermal administration, intravenous administration, intramuscular administration, subcutaneous injection, and intracerebral administration routes.

The pharmaceutical composition of the present invention can be formulated with one or more pharmaceutically acceptable carriers that are generally used in the art. The pharmaceutically acceptable carriers are carriers for parenteral administration, for example, water, suitable oils, saline solutions, aqueous glucose, and glycol. The pharmaceutical composition of the present invention may further include a stabilizer and a preservative. Suitable stabilizers are antioxidants such as sodium bisulfite, sodium sulfite, and ascorbic acid. Suitable preservatives are benzalkonium chloride, methyl paraben, propyl paraben, and chlorobutanol. The pharmaceutical composition of the present invention may optionally further include a suspending agent, a dissolution aid, a stabilizer, an isotonic agent, a preservative, an adsorption inhibitor, a surfactant, a diluent, an excipient, a pH-adjusting agent, an analgesic, a buffer or an antioxidant depending on the administration mode and formulation. Details of other suitable pharmaceutically acceptable carriers and formulations can be found in *Remington's Pharmaceutical Sciences* (the newest edition).

The pharmaceutical composition of the present invention can be formulated with one or more pharmaceutically acceptable carriers and/or excipients in accordance with methods that can be easily carried out by those skilled in the art. The pharmaceutical composition can be provided in unit dosage forms or dispensed in multi-dose containers.

The pharmaceutical composition may be administered using any device capable of transferring the active ingredient to target cells. The pharmaceutical composition may be used in a therapeutically effective amount for the treatment of the target disease. As used herein, the term "treatment" or "treating" means to reverse or alleviate one or more symptoms of a disease or illness in need of treatment or to inhibit or prevent the progress of the symptoms, unless otherwise mentioned. The term "therapeutically effective amount" means the amount of the active ingredient or the pharmaceutical composition that induces a biological or medical response in a tissue system, animal or human, as determined by researchers, veterinarians, doctors or other clinicians. The term is intended to include an amount that induces relief of symptoms of the disease or disorder in question. It is obvious to those skilled in the art that the effective amount of the active ingredient in the pharmaceutical composition will vary depending on the desired effect.

Therefore, the optimum amount of the pharmaceutical composition can be easily determined by those skilled in the art and may vary depending on various factors, including type and severity of the disease, amounts of other ingredients in the composition, type of the formulation, patient's age, weight, general health, sex, and diet, time and route of administration, secretion rate of the composition, treatment period, and presence of a concomitant drug.

In consideration of these factors, it is important to determine the amount of the composition that can achieve the maximum effects from the smallest amount without side effects. For example, the composition of the present invention may be administered in such an amount that cells transformed with the vector containing the SYNCRIP gene as the active ingredient are $0.1 \times 10^5$ to $1.0 \times 10^8$ cells/kg (body weight), more preferably $0.5 \times 10^6$ to $1.0 \times 10^7$ cells/kg (body weight). However, the dose of the composition may be prescribed depending on various factors such as formulation, mode of administration, patient's age, weight, sex, pathological condition, and diet, time and route of administration, excretion rate, and responsiveness and those skilled in the art can suitably adjust the dose in consideration of these factors. The composition is administered only once. Alternatively, the composition may be administered twice or more within the range of clinically acceptable side effects.

The composition may be administered to one or more sites. The same dose per kg can apply to animals other than human beings. Alternatively, the composition may be administered in an amount obtained by converting the dose based on, for example, the volume ratio (e.g., average value) of the ischemic organs (e.g., heart) of the subject animal to those of human. Examples of animals to be treated according to the present invention include humans and other mammals, specifically monkeys, mice, rats, rabbits, sheep, cows, dogs, goats, horses, and pigs.

The present invention will be explained in more detail with reference to the following examples. However, these examples are not to be construed as limiting or restricting the scope and disclosure of the invention. It is to be understood that based on the teachings of the present invention including the following examples, those skilled in the art can readily practice other embodiments of the present invention whose experimental results are not explicitly presented. Such modifications and variations are intended to come within the scope of the appended claims.

The experimental results of the following examples, including comparative examples, are merely representative and the effects of the exemplary embodiments of the present invention that are not explicitly presented hereinafter can be specifically found in the corresponding sections.

Experimental Example 1. Validation of Biomarker for Drug Addiction

1) Drug Addiction Animal Model (MA)

In this experiment, C57BL/6J mice aged 7 weeks or older were prepared as experimental animals. The experimental animals had ad libitum access to diet and water. All procedures were performed with the approval of the Institutional Animal Care and Use Committee of the Korea Institute of Science and Technology. The experimental animals were acclimated to the laboratory environment for one week. The animals were observed for general behavioral changes. Animals with abnormalities were excluded from this experiment. All experimental animals were housed with a 12-h light/dark cycle and had ad libitum access to water and food in cages under controlled temperature and humidity.

A control group and a drug addiction animal model were prepared as follows. 8 animals were randomly assigned to each group. A drug addiction animal model was prepared by the following procedure. First, the animals were addicted to methamphetamine according to a gradual ramp-up protocol. Specifically, 0.5-1.5 mg/kg of methamphetamine was injected once a day for the first 3 days of the first week (day 1-3), 1.5-2.5 mg/kg of methamphetamine was injected twice a day for the next 3 days (day 4-6), the methamphetamine injection was stopped for one day, and 2.5-4.0 mg/kg of methamphetamine was injected three times a day for 6 days of the second week (day 8-13). Then, the injection was stopped for one week.

A control group was prepared by intraperitoneally injecting 10 ml/kg of sterile saline instead of methamphetamine repeatedly at the same time for 2 weeks and stopping the injection for the next one week.

2) Expression Analysis of Biomarker miR-137 Associated with Drug Addiction cDNA was prepared through reverse transcription. To this end, the control group and the drug addiction animal model were anesthetized, and their heads were cut off to collect striatum and serum samples. A total of 50 ng of RNA was extracted from the samples. For miRNA, cDNA was amplified using TaqMan Universal Master Mix II (Thermo Fisher Scientific) without uracil- DNA glycosylase (UNG) according to the manufacturer's protocol. Next, the expression of mature miRNA was quantified by quantitative real-time PCR (qPCR) with TaqMan MicroRNA Assays (Thermo Fisher Scientific). The qPCR was performed in CFX Connect (Bio-Rad). All reactions were measured in triplicate.

The relative abundance of miRNA and mRNA measured from the above results was confirmed by the $2^{-ddCt}$ method. snoRNA202 was used as a normalized control to quantify miRNA present in the mouse brain. Standard miRNA miR-16 was used as a normalized control to quantify miRNA present in the serum.

FIG. 1 compares the expression levels of miR137 in the serum and brain striatum samples from the control group (Control) and the drug addiction animal model (MA). Referring to FIG. 1, the expression levels of miR-137 in the striatum samples from the drug addiction animal model (MA) addicted to methamphetamine were significantly high compared to those in the striatum samples from the control group (Control).

The expression levels of miR-137 in the serum samples from the drug addiction animal model (MA) addicted to methamphetamine were significantly low compared to those in the striatum samples from the control group (Control). The expression levels of miR-137 were confirmed by qPCR.

This tendency demonstrates that miR-137 acts as a biomarker capable of diagnosing drug addiction and withdrawal symptoms due to drug addiction. Therefore, the fact is again confirmed that miR-137 acts as a biomarker for determining the presence of drug addiction and withdrawal symptoms due to drug addiction.

Experimental Example 2. Confirmation of the Mutual Influence of miR-137 and SYNCRIP A miRNA 3'UTR target expression clone for mouse Syncrip NM_019666.2 (SYNCRIP-3'UTR) (MmiT031985-MT05, GeneCopoeia), human pre-microRNA expression construct Lenti-miR-137 (PMIRH137PA-1, System Biosciences), and a control vector for luciferase analysis were prepared.

Luciferase analysis was conducted according to the manufacturer's protocol. Briefly, first, HEK293TN cells were cultured in a 12-well cell culture plate using EndoFectin Lenti transfection reagent (GeneCopoeia) and co-transfected with SYNCRIP-3'UTR and a miR-137 overexpression vector (or a scrambled control vector). The medium was changed after 16 h and collected after 32 h.

For each cell, the activity of Gaussia luciferase (GL) was normalized to the activity of alkaline phosphatase (AP) using the Secrete-Pair Dual Luminescence Assay Kit (GeneCopoeia) according to the manufacturer's protocol. The activity of each enzyme was quantified by reading the absorbance using a Synergy HTX Multi-Mode Microplate Reader (BioTek, VT, USA).

Figure 2:
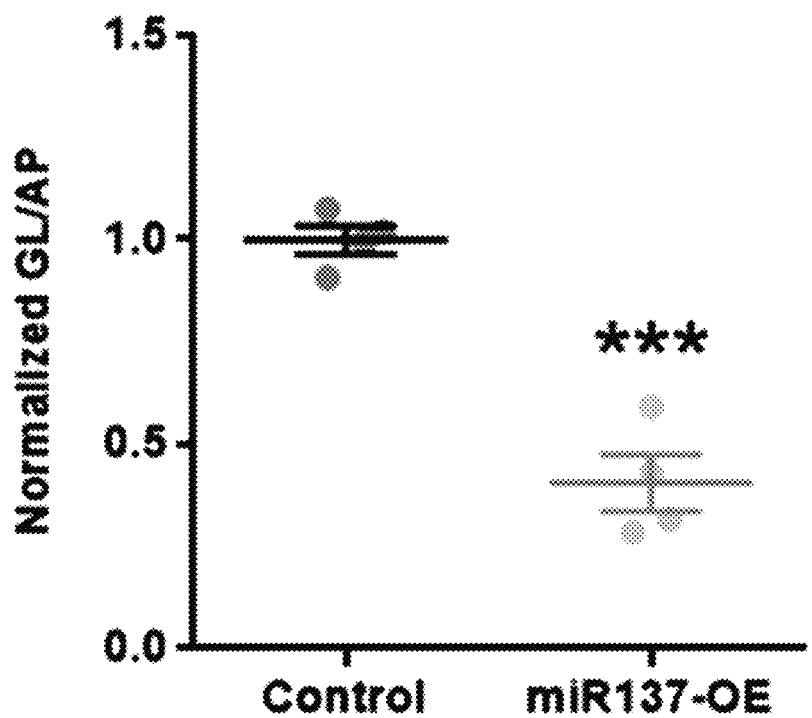
FIG. 2 shows the quantified GL/AP activities in HEK293TN cells transfected with SYNCRIP-3'UTR and a miR-137 overexpression vector (miR137-OE) and HEK293TN cells transfected with SYNCRIP-3'UTR and a scrambled control vector (Control)

FIG. 2 shows the quantified GL/AP activities in the HEK293TN cells transfected with SYNCRIP-3'UTR and a miR-137 overexpression vector (miR137-OE) and the HEK293TN cells transfected with SYNCRIP-3'UTR and a scrambled control vector (Control).

As shown in FIG. 2, the GL/AP was significantly reduced in the miR-137 overexpressed cells (miR137-OE), indicating that miR-137 binds to SYNCRIP mRNA to inhibit the expression of the SYNCRIP gene.

Experimental Example 3. Confirmation of Effect of SYNCRIP on Drug Addiction

1) Preparation of Drug Addiction Animal Model

C57BL/6J mice aged 7 weeks or older were purchased from the Laboratory Animal Resource Center, Korea Institute of Science and Technology and used as experimental animals. All procedures were performed with the approval of the Institutional Animal Care and Use Committee of the Korea Institute of Science and Technology. The experimental animals were acclimated to the laboratory environment for at least one week prior to the procedure. The animals were observed for general behavioral changes. Animals with abnormalities were excluded from this experiment. All experimental animals were housed with a 12-h light/dark cycle and had ad libitum access to water and food in cages under controlled temperature and humidity.

A drug addiction animal model was prepared by the following procedure. First, the animals were addicted to methamphetamine according to a gradual ramp-up protocol. Specifically, 0.5-1.5 mg/kg of methamphetamine was injected once a day for the first 3 days of the first week (day 1-3), 1.5-2.5 mg/kg of methamphetamine was injected twice a day for the next 3 days (day 4-6), the methamphetamine injection was stopped for one day, and 2.5-4.0 mg/kg of methamphetamine was injected three times a day for 6 days of the second week (day 8-13). Then, the injection was stopped for one week.

A control group was prepared by intraperitoneally injecting 10 ml/kg of sterile saline instead of methamphetamine repeatedly at the same time for 2 weeks and stopping the injection for the next one week.

2) Analysis of SYNCRIP Expression (Western Blotting)

The control group and the drug addiction animal model were anesthetized and their heads were cut off to collect striatum samples. Proteins were extracted from the striatum (hereinafter also referred to as "brain") using RIPA buffer (Thermo Fisher Scientific). The extraction process was carried out according to the manufacturer's protocol. The concentration of the proteins in the extracted protein sample was quantified through a Protein Assay Dye Reagent Concentrate (Bio-Rad) and a spectrophotometer.

First, the protein (50 μg/lane) sample was loaded on SDS-PAGE and transferred to a PVDF membrane. The PVDF membrane was treated with 5% skim-milk for 20 min, washed, and treated with primary antibodies at 4° C., allowed to react overnight, and incubated at room temperature for 2 h. Rabbit anti-hnRNP Q (1:10,000) (ab184946, Abcam, Cambridge, UK) and mouse anti-β-actin (1:500) (sc-47778, Santa Cruz Biotechnology, CA, USA) were used as the primary antibodies.

Subsequently, the membrane bound with the primary antibodies was washed and donkey anti-rabbit IgG-HRP (1:2,000) (sc-2317, Santa Cruz Biotechnology) or donkey anti-mouse IgG-HRP (1:2,000) (sc-2318, Santa Cruz Biotechnology) was incubated at room temperature for 2 h. HRP signals were visualized using SuperSignal West Pico Chemiluminescent Substrate (Thermo Fisher Scientific) and Image Quant LAS4000 (GE Healthcare Bio-Sciences, Uppsala, Sweden).

Image J was used for quantitative densitometric comparison. In this experiment, the samples were treated correspondingly from the blots for the same samples and the detection of the loading control ((3-actin) was performed in the same blot as a target (SYNCRIP).

3) Expression Levels of SYNCRIP (qPCR)

cDNA was prepared through reverse transcription. To this end, the control group (Control) and the drug addiction animal model (MA) were anesthetized, and their heads were cut off to collect striatum and serum samples. A total of 50 ng of RNA was extracted from the samples. For miRNA, cDNA was amplified using TaqMan Universal Master Mix II (Thermo Fisher Scientific) without UNG according to the manufacturer's protocol. Next, the expression of mature miRNA was quantified by quantitative real-time PCR (qPCR) with TaqMan MicroRNA Assays (Thermo Fisher Scientific). The qPCR was performed in CFX Connect (Bio-Rad). All reactions were measured in triplicate.

The relative abundance of miRNA and mRNA measured from the above results was confirmed by the $2^{-ddCt}$ method. snoRNA202 was used as a normalized control to quantify miRNA present in the mouse brain. Standard miRNA miR-16 was used as a normalized control to quantify miRNA present in the serum.

Figure 3:
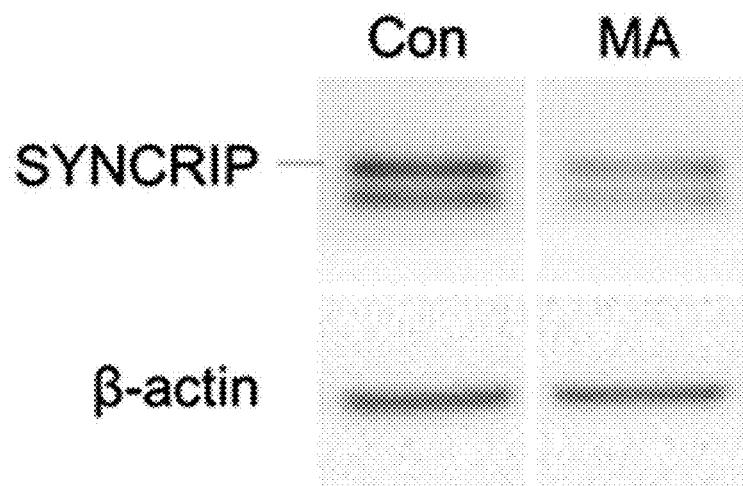
FIG. 3 shows the expression levels of SYNCRIP in brain striatum samples from a control group and a drug addiction animal model, which were analyzed by Western blotting.

FIG. 3 shows the expression levels of SYNCRIP in the brain striatum samples from the control group and the drug addiction animal model. The expression levels were analyzed by Western blotting. Referring to FIG. 3, the expression level of SYNCRIP in the brain striatum of the animal model (MA) addicted to methamphetamine as a result of abuse decreased to a significantly lower level than that in the control group. That is, drug addiction significantly decreased the expression level of SYNCRIP.

Figure 4:
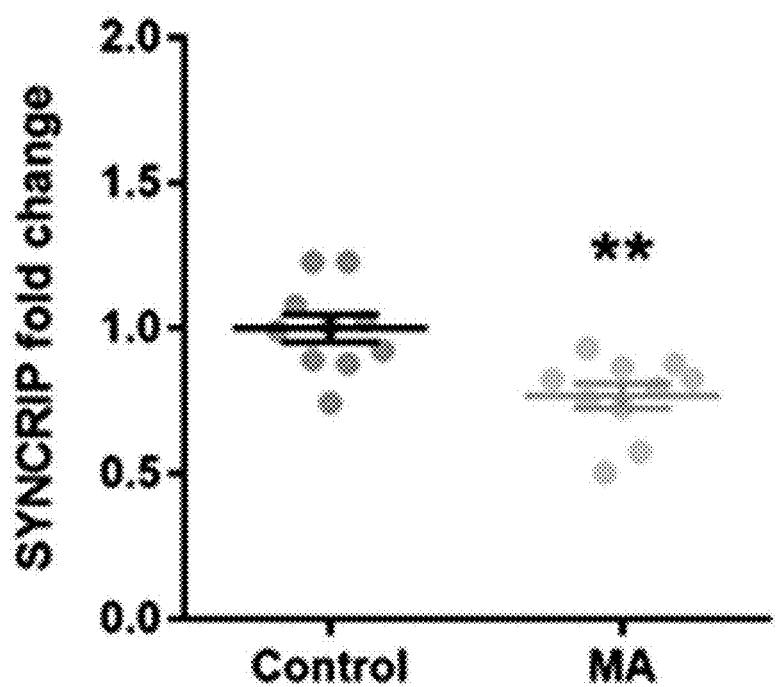
FIG. 4 compares the expression levels of SYNCRIP in brain striatum samples from a control group and a drug addiction animal model.

FIG. 4 compares the expression levels of SYNCRIP in the brain striatum samples from the control group and the drug addiction animal model. Referring to FIG. 4, the expression level of SYNCRIP in the brain striatum of the drug addiction animal model (MA) addicted to methamphetamine decreased but was significantly higher than that in the control group. These results demonstrate the availability of the SYNCRIP gene as a biomarker for drug addiction.

Experimental Example 4. Confirmation of Effect of SYNCRIP on Expression Level of miR-137

The following experiment was conducted to confirm that the marker for drug addiction increased when SYNCRIP was overexpressed in neurons.

Figure 5:
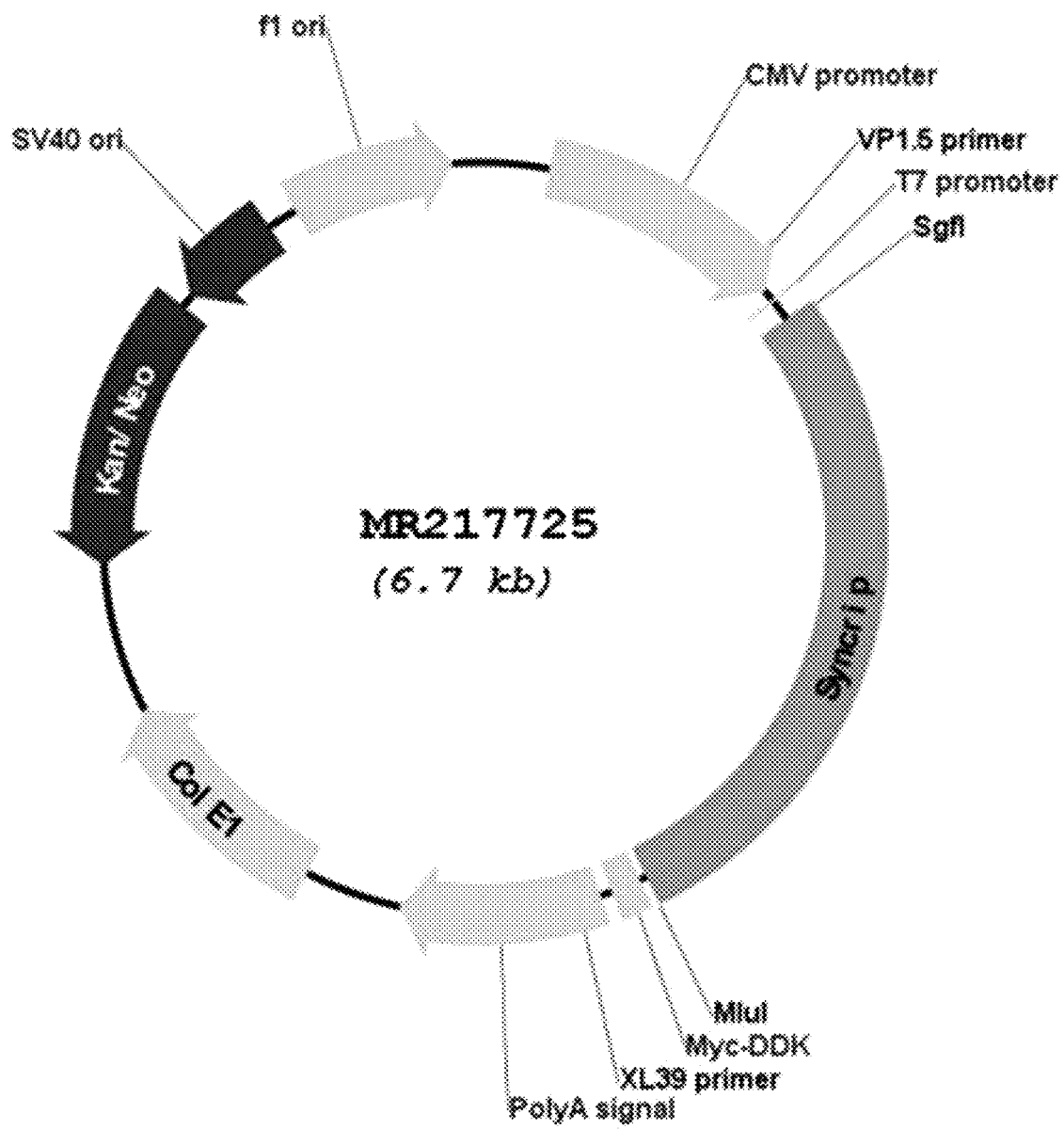
FIG. 5 is a cleavage map of a SYNCRIP overexpression vector (Syncrip (NM_019666) Mouse Tagged ORF Clone vector (MR217725L4, OriGene Technologies, MD, USA))

First, SH-SY5Y neurons were purchased from the Korean Cell Line Bank, plated in a 100 ø dish, and cultured in a $CO_2$ incubator for cell culture at 37° C. Thereafter, Syncrip (NM_019666) Mouse Tagged ORF Clone vector (MR217725L4, OriGene Technologies, MD, USA) was used to overexpress SYNCRIP in the neurons (FIG. 5).

In this experiment, pLenti-C-mGFP-P2A-Puro vector (OriGene Technologies) was used as a control.

cDNA was prepared through reverse transcription. To this end, a total of 50 ng of RNA was extracted from the samples. For miRNA, cDNA was amplified using TaqMan Universal Master Mix II (Thermo Fisher Scientific) without UNG according to the manufacturer's protocol. Next, the expression of mature miRNA was quantified by quantitative real-time PCR (qPCR) with TaqMan MicroRNA Assays (Thermo Fisher Scientific). The qPCR was performed in CFX Connect (Bio-Rad). All reactions were measured in triplicate.

The relative abundance of miRNA and mRNA measured from the above results was confirmed by the $2^{-ddCt}$ method. snoRNA202 was used as a normalized control to quantify miRNA present in the mouse brain. Standard miRNA miR-16 was used as a normalized control to quantify miRNA present in the serum.

Figure 6:
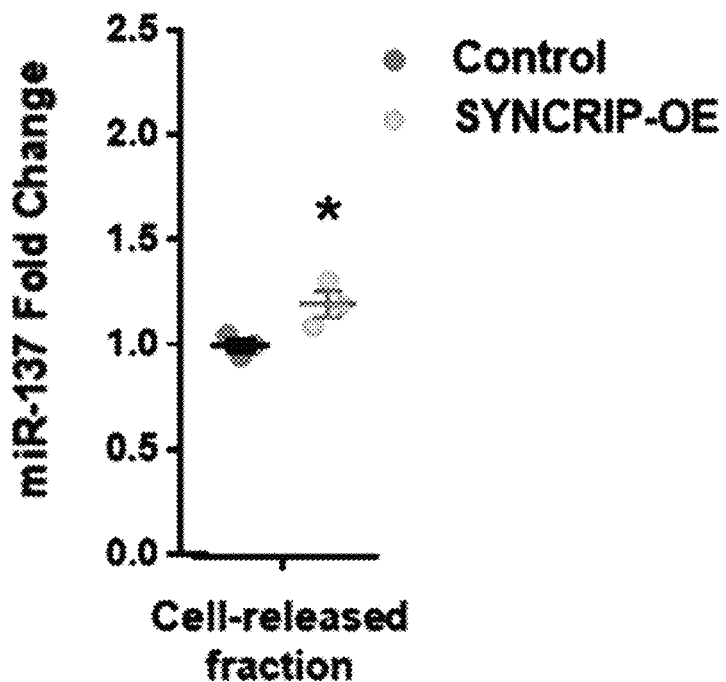
FIG. 6 compares the expression levels of miR-137 secreted from a SYNCRIP overexpressing neuronal cell line (SYNCRIP-OE) and a control group (Control)

FIG. 6 compares the expression levels of miR-137 secreted from the SYNCRIP overexpressing neuronal cell line (SYNCRIP-OE) and the control group (Control). Referring to FIG. 6, when the SYNCRIP gene was overexpressed in the cultured cell line, the expression level of the drug addiction marker gene miR-137 secreted from the cells was also significantly increased, which was confirmed through qPCR. This indicates that SYNCRIP overexpression in neurons can increase the secretion of the marker miR-137 due to drug addiction, demonstrating that the secretion of miR-137, a biomarker for drug addiction, can be upregulated through the SYNCRIP gene. In conclusion, a therapeutic agent applicable to the treatment and prevention of drug addiction can be screened based on the expression level of the SYNCRIP gene, suggesting that an agent promoting the SYNCRIP gene can be applied as a therapeutic agent.

Experimental Example 5. Validation of SYNCRIP—1

1) Preparation of Drug Addiction Animal Model (MA) and Drug-Addicted Transgenic Animal Model ($DST^{SYNCRIP-OE}$+MA)

C57BL/6J male mice aged 7 weeks or older were purchased from the Laboratory Animal Resource Center, Korea Institute of Science and Technology and used as experimental animals. All procedures were performed with the approval of the Institutional Animal Care and Use Committee of the Korea Institute of Science and Technology. The experimental animals were acclimated to the laboratory environment for at least one week prior to the procedure. The animals were observed for general behavioral changes. Animals with abnormalities were excluded from this experiment. All experimental animals were housed with a 12-h light/dark cycle and had ad libitum access to water and food in cages under controlled temperature and humidity.

For an animal experiment, a lentiviral system was established for easy synthesis of SYNCRIP transcript and long-term expression. Specifically, Syncrip (NM_019666) Mouse Tagged ORF Clone vector (MR217725L4, OriGene Technologies, MD, USA) and pLenti-C-mGFP-P2A-Puro vector (OriGene Technologies) as its control were packaged with lentivirus before use (FIG. 5).

The experimental animals were anesthetized with a ketamine-xylazine mixture (ketamine 120 mg/kg, xylazine 8 mg/kg) before opening the scalp and trepanation. Holes were made into the skull using coordinates from bregma: AP+1.1, ML±1.65 mm. Thereafter, 0.2, 0.7, and 0.7 μl of lentivirus were injected into coordinates DV −3.0, −2.6, and −2.2 mm, respectively. The injected virus specifically targeted only the cholinergic interneurons of the striatum by Cre-lox recombination. After lentivirus injection, the holes were closed with silk sutures. The animals were stabilized and infected with the virus for 4 weeks post-surgery. The infected animals were used as a SYNCRIP overexpressing transgenic animal model ($DST^{SYNCRIP-OE}$).

Small amounts of methamphetamine were injected into the transgenic animal model ($DST^{SYNCRIP-OE}$) for a long period of time (abuse) to induce a mild drug addiction state (a hyper-excited state without any symptoms). Specifically, the mild drug-addicted transgenic animal model ($DST^{SYNCRIP-OE}$+MA) was prepared by intraperitoneally injecting 1.0 mg/kg of methamphetamine once every other day for 2 weeks.

A control group was prepared by intraperitoneally injecting 10 ml/kg of sterile saline instead of methamphetamine into a control animal model instead of the transgenic animal model. The control animal model was prepared by treatment with the same amount of pLenti-C-mGFP-P2A-Puro lentivirus that does not express SYNCRIP. The sterile saline was repeatedly at the same time once every other day for 2 weeks.

A drug addiction animal model (MA) was prepared following the above addiction procedure, except that non-transgenic general animals were used. The drug addiction animal model (MA) was used as a comparative group.

2) Expression Analysis of Biomarker miR-137 Associated with Drug Addiction cDNA was prepared through reverse transcription. To this end, the control group, the drug addiction animal model, and the drug-addicted transgenic animal model were anesthetized, and their serum samples were collected. A total of 50 ng of RNA was extracted from the samples. For miRNA, cDNA was amplified using TaqMan Universal Master Mix II (Thermo Fisher Scientific) without UNG according to the manufacturer's protocol. Next, the expression of mature miRNA was quantified by quantitative real-time PCR (qPCR) with TaqMan MicroRNA Assays (Thermo Fisher Scientific). The qPCR was performed in CFX Connect (Bio-Rad). All reactions were measured in triplicate.

The relative abundance of miRNA and mRNA measured from the above results was confirmed by the $2^{-ddCt}$ method. snoRNA202 was used as a normalized control to quantify miRNA present in the mouse brain. Standard miRNA miR-16 was used as a normalized control to quantify miRNA present in the serum.

Figure 7:
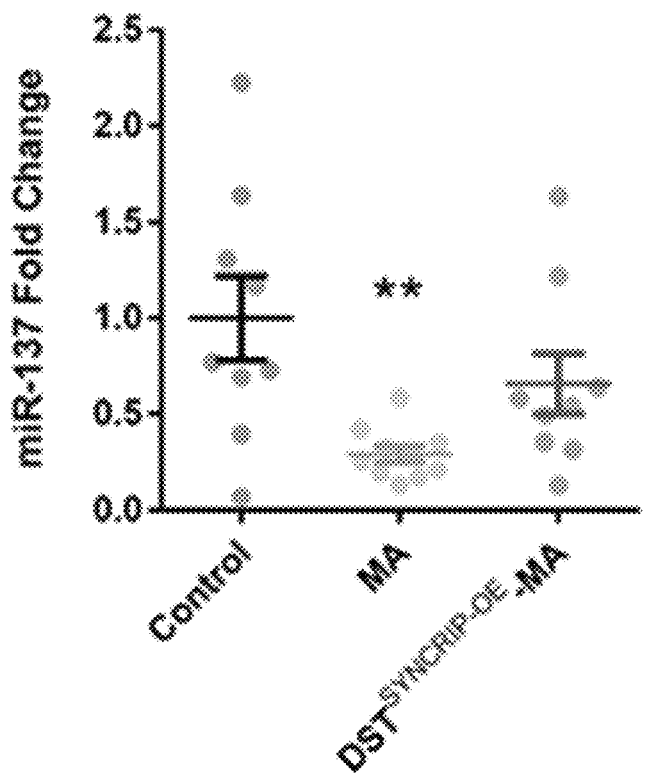
FIG. 7 shows the expression levels of miR-137, a biomarker for drug addiction, in a mild drug-addicted transgenic animal model with increased SYNCRIP expression in the striatum ($DST^{SYNCRIP-OE}$-MA), a normal group (Control), and a drug addiction animal model (MA), which were measured by qPCR.

FIG. 7 shows the expression levels of miR-137, a biomarker for drug addiction, in the mild drug-addicted transgenic animal model with increased SYNCRIP expression in the striatum ($DST^{SYNCRIP-OE}$-MA), the normal group (Control), and the drug addiction animal model (MA), which were measured by qPCR.

As shown in FIG. 7, the expression level of serum miR-137 was decreased even in the mild drug addiction animal model (MA) prepared by repeated administration of methamphetamine at a low concentration to induce a mild drug addiction state. Specifically, the expression level of miR-137 in the mild drug addiction animal model (MA) was significantly low compared to that in the control group, which was confirmed by qPCR.

These results reveal that drug addiction with mild withdrawal symptoms as well as drug addiction with severe withdrawal symptoms can be detected through the expression levels of miR-137 in blood. Therefore, it can be concluded that miR-137 is a major biomarker capable of diagnosing drug addiction, as previously known in the art. As the expression of SYNCRIP in the striatum of the drug addiction animal model ($DST^{SYNCRIP-OE}$-MA) increased, the expression level of miR-137, a marker for drug addiction, in blood increased compared to that in the MA group and was restored to a level that was not significantly different from that in the control group. These expression levels were confirmed by qPCR. Overexpression of SYNCRIP in neurons can lead to the recovery of the mild drug addiction without withdrawal symptoms to an extent similar to the normal group. In conclusion, the SYNCRIP gene enables the diagnosis of mild drug addiction without withdrawal symptoms as well as severe drug addiction with withdrawal symptoms and can be used as a biomarker for screening a therapeutic agent. In addition, an agent expressing SYNCRIP or promoting the activity of SYNCRIP can be used in a pharmaceutical composition for treating drug addiction.

Experimental Example 6. Validation of SYNCRIP—2

1) Preparation of Drug-Addicted Transgenic Animal Model (Brain$^{SYNCRIP-OE}$+MA)

C57BL/6J male mice aged 7 weeks or older were purchased from the Laboratory Animal Resource Center, Korea Institute of Science and Technology and used as experimental animals. All procedures were performed with the approval of the Institutional Animal Care and Use Committee of the Korea Institute of Science and Technology. The experimental animals were acclimated to the laboratory environment for at least one week prior to the procedure. The animals were observed for general behavioral changes. Animals with abnormalities were excluded from this experiment. All experimental animals were housed with a 12-h light/dark cycle and had ad libitum access to water and food in cages under controlled temperature and humidity.

For an animal experiment, a lentiviral system was established for easy synthesis of SYNCRIP transcript and long-term expression. Specifically, Syncrip (NM_019666) Mouse Tagged ORF Clone vector (MR217725L4, OriGene Technologies, MD, USA) (FIG. 5) and pLenti-C-mGFP-P2A-Puro vector (OriGene Technologies) as its control were packaged with lentivirus before use.

The experimental animals were anesthetized with a ketamine-xylazine mixture (ketamine 120 mg/kg, xylazine 8 mg/kg) before opening the scalp and trepanation. Holes were made into the skull using coordinates from bregma: AP+1.1, ML±1.65 mm. Thereafter, 0.2, 0.7, and 0.7 µl of lentivirus were injected into coordinates DV −3.0, −2.6, and −2.2 mm, respectively. The injected virus specifically targeted only the cholinergic interneurons of the striatum by Cre-lox recombination. After lentivirus injection, the holes were closed with silk sutures. The animals were stabilized and infected with the virus for 4 weeks post-surgery. The infected animals were used as a SYNCRIP overexpressing transgenic animal model ($DST^{SYNCRIP-OE}$).

A transgenic animal model ($DST^{SYNCRIP-OE}$+MA) was prepared by the following procedure. First, the transgenic animal model ($DST^{SYNCRIP-OE}$) was addicted to methamphetamine according to a gradual ramp-up protocol. Specifically, 0.5-1.5 mg/kg of methamphetamine was injected once a day for the first 3 days of the first week (day 1-3), 1.5-2.5 mg/kg of methamphetamine was injected twice a day for the next 3 days (day 4-6), the methamphetamine injection was stopped for one day, and 2.5-4.0 mg/kg of methamphetamine was injected three times a day for 6 days of the second week (day 8-13). Then, the injection was stopped for one week.

A control group was prepared by intraperitoneally injecting 10 ml/kg of sterile saline instead of methamphetamine into a control animal model instead of the transgenic animal model. The control animal model was prepared by treatment with the same amount of pLenti-C-mGFP-P2A-Puro lentivirus that does not express SYNCRIP. The sterile saline was repeatedly at the same time for 4 weeks. A drug addiction animal model (MA) was prepared following the above addiction procedure, except that non-transgenic general animals were used. The drug addiction animal model (MA) was used as a comparative group.

2) Expression Analysis of Biomarker miR-137 Associated with Drug Addiction cDNA was prepared through reverse transcription. To this end, the control group and the drug-addicted transgenic animal model (experimental group) were anesthetized, and their serum samples were collected. A total of 50 ng of RNA was extracted from the samples. For miRNA, cDNA was amplified using TaqMan Universal Master Mix II (Thermo Fisher Scientific) without UNG according to the manufacturer's protocol. Next, the expression of mature miRNA was quantified by quantitative real-time PCR (qPCR) with TaqMan MicroRNA Assays (Thermo Fisher Scientific). The qPCR was performed in CFX Connect (Bio-Rad). All reactions were measured in triplicate.

The relative abundance of miRNA and mRNA measured from the above results was confirmed by the $2^{-ddCt}$ method. snoRNA202 was used as a normalized control to quantify miRNA present in the mouse brain. Standard miRNA miR-16 was used as a normalized control to quantify miRNA present in the serum.

Figure 8:
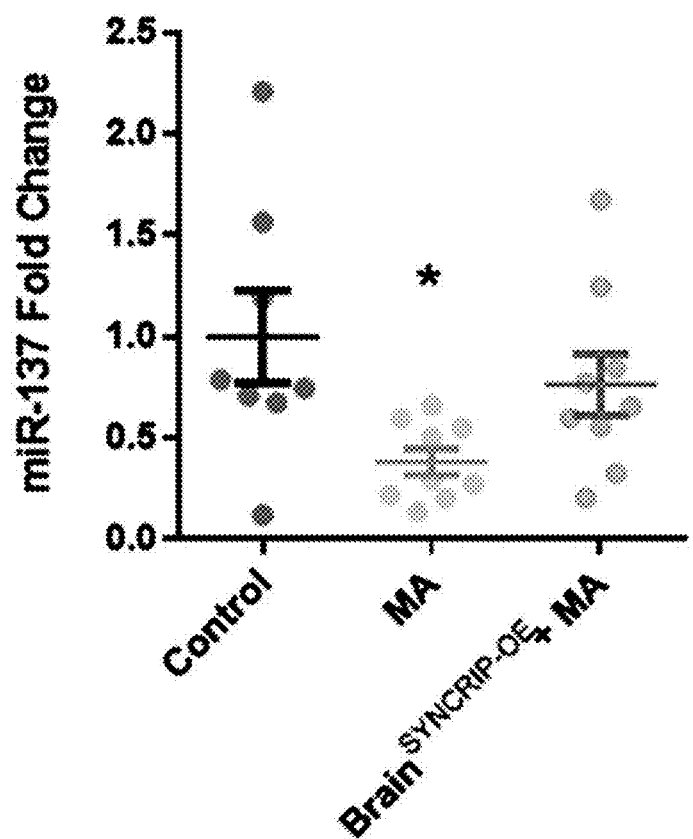
FIG. 8 shows the expression levels of miR-137, a biomarker for drug addiction, in a drug-addicted transgenic animal model with increased SYNCRIP expression in the striatum ($Brain^{SYNCRIP-OE}$) a normal group (Control), and a drug addiction animal model (MA), which were measured by qPCR.

FIG. 8 shows the expression levels of miR-137, a biomarker for drug addiction, in the transgenic animal model with increased SYNCRIP expression in the striatum (Brain$^{SYNCRIP-OE}$-MA), the normal group (Control), and the drug addiction animal model (MA). These expression levels were measured by qPCR.

As shown in FIG. 8, the expression level of miR-137 in the serum of the comparative group (MA) addicted to simple methamphetamine was significantly reduced compared to that in the control group. These results again demonstrate that drug addiction such as methamphetamine addiction can be diagnosed based on a reduction in the level of miR-137 in serum.

In addition, the expression of miR-137, a marker gene for drug addiction, in the serum of the SYNCRIP overexpressed transgenic animal model (Brain$^{SYNCRIP-OE}$+MA) was restored to a normal level, indicating that the use of SYNCRIP enables the prevention or treatment of drug addiction.

Experimental Example 7. Therapeutic Efficacy of SYNCRIP on Animal Model with Withdrawal Symptoms Caused by Methamphetamine 1) Preparation of Drug Addiction Animal Model C57BL/6J mice aged 7 weeks or older were purchased from the Laboratory Animal Resource Center, Korea Institute of Science and Technology and used as experimental animals. All procedures were performed with the approval of the Institutional Animal Care and Use Committee of the Korea Institute of Science and Technology. The experimental animals were acclimated to the laboratory environment for at least one week prior to the procedure. The animals were observed for general behavioral changes. Animals with abnormalities were excluded from this experiment. All experimental animals were housed with a 12-h light/dark cycle and had ad libitum access to water and food in cages under controlled temperature and humidity.

A drug addiction animal model was prepared by the following procedure. First, the animals were addicted to methamphetamine according to a gradual ramp-up protocol. Specifically, 0.5-1.5 mg/kg of methamphetamine was injected once a day for the first 3 days of the first week (day 1-3), 1.5-2.5 mg/kg of methamphetamine was injected twice a day for the next 3 days (day 4-6), the methamphetamine injection was stopped for one day, and 2.5-4.0 mg/kg of methamphetamine was injected three times a day for 6 days of the second week (day 8-13). Then, the injection was stopped for one week.

A control group was prepared by intraperitoneally injecting 10 ml/kg of sterile saline instead of methamphetamine repeatedly at the same time for 2 weeks and stopping the injection for the next one week.

2) Induction of SYNCRIP Overexpression in the Drug Addiction Animal Model (MA)

A determination was made as to whether SYNCRIP treatment showed a therapeutic effect on the animal model (MA) with withdrawal symptoms due to drug addiction. To this end, a lentivirus capable of overexpressing Syncrip (NM_019666) Mouse Tagged ORF Clone vector (MR217725L4, OriGene Technologies, MD, USA) was injected into the brain striatum of the drug addiction animal model (MA) prepared in step 1) (FIG. 5). Specifically, the drug addiction animal model (MA) was anesthetized with a ketamine-xylazine mixture (ketamine 120 mg/kg, xylazine 8 mg/kg) before opening the scalp and trepanation. Holes were made into the skull using coordinates from bregma: AP+1.1, ML±1.65 mm. Thereafter, 0.2, 0.7, and 0.7 μl of lentivirus were injected into coordinates DV −3.0, −2.6, and −2.2 mm, respectively. After lentivirus injection, the holes were closed with silk sutures. The animals were stabilized and infected with the virus for 4 weeks post-surgery. The infected animals were used as an animal model in which SYNCRIP overexpression was induced after drug addiction (MA-SYNCRIP; Experimental group). All experimental animals were housed with a 12-h light/dark cycle and had ad libitum access to water and food in cages under controlled temperature and humidity.

3) Evaluation of Egocentric Spatial Learning of the Drug Addiction Animal Model (MA), the Control Group, and the Animal Model in which SYNCRIP Overexpression was Induced after Drug Addiction (MA-SYNCRIP; Experimental Group)

The drug addiction animal model (MA), the control group, and the animal model in which SYNCRIP overexpression was induced after drug addiction (MA-SYNCRIP; experimental group) were evaluated for cognitive dysfunction, one of the typical symptoms of drug addiction, using a water cross maze.

Figure 9:
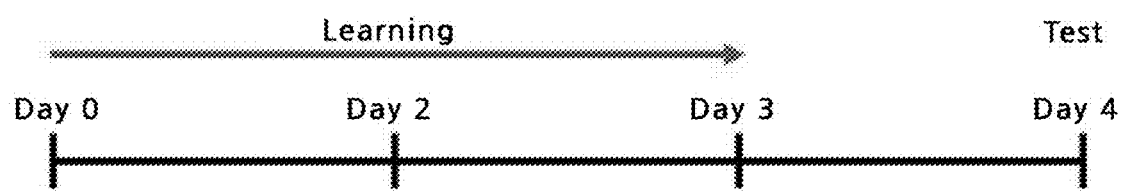
FIG. 9 schematically shows a test schedule designed for evaluating egocentric spatial learning behaviors using a water cross maze.
Figure 10:
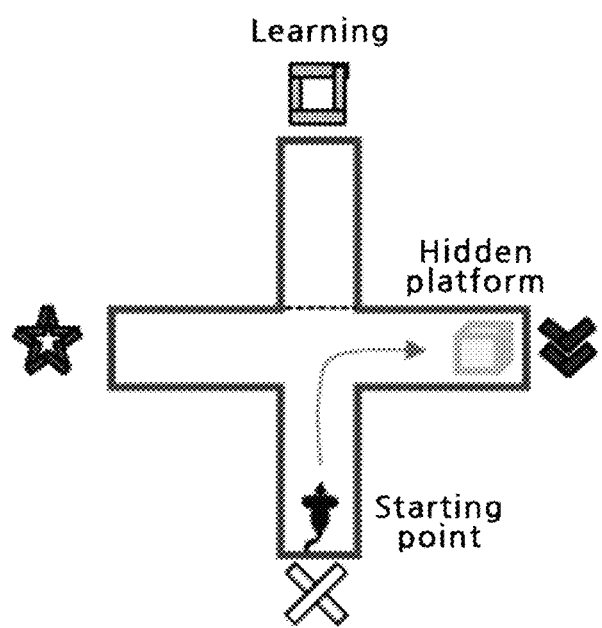
FIG. 10 shows the structure of a water cross maze during the spatial learning period in order to evaluate behaviors caused by drug addiction.

The water cross maze is a cruciform maze that has four open branches (each 30×6 cm) and is filled with water up to 10 cm above the floor. A hidden platform was placed in the right branch when viewed from the starting point of the water cross maze. The experimental animal was placed at the starting point and allowed to freely find the hidden platform for 5 min. If the experimental animal failed to find the platform within 5 min, it was guided directly to the platform to learn the location of the platform. The learning process was repeated 6 times a day for a total of 3 days. The learning process was performed at intervals of 10 min, 10 min, 3 h, 10 min, and 10 min within a day (FIGS. 9 and 10).

Figure 11:
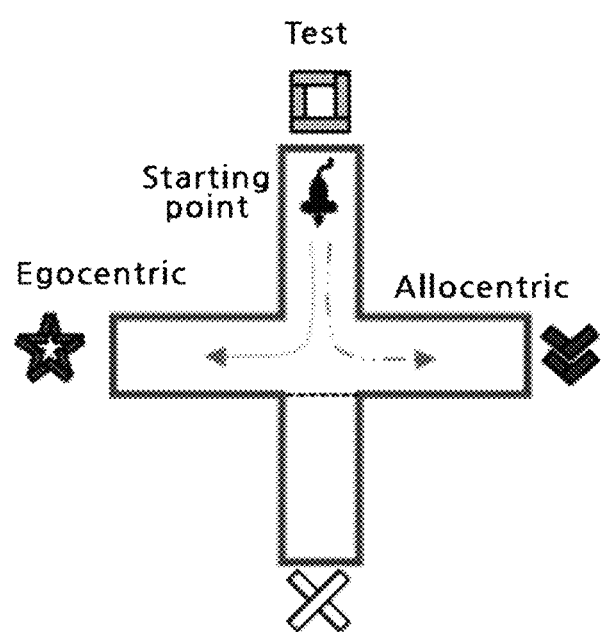
FIG. 11 shows the structure of a water cross maze designed to evaluate spatial learning after the learning period in order to evaluate behaviors caused by drug addiction.

On the next day after learning for 3 days, a probe test was conducted (FIG. 11). For this test, the experimental animal was placed in the branch opposite the starting point, which had been used during the learning period, and was then allowed to find the platform depending on visual cues. The experimental animal was evaluated to perform allocentric spatial learning if it went to the platform marked with ⌣. Meanwhile, the experimental animal was evaluated to perform egocentric spatial learning if it went to the right side (the branch marked with asterisk) that had been learned during the learning period. The number of mice having performed egocentric spatial learning was measured, and expressed in percent, and plotted.

Figure 12:
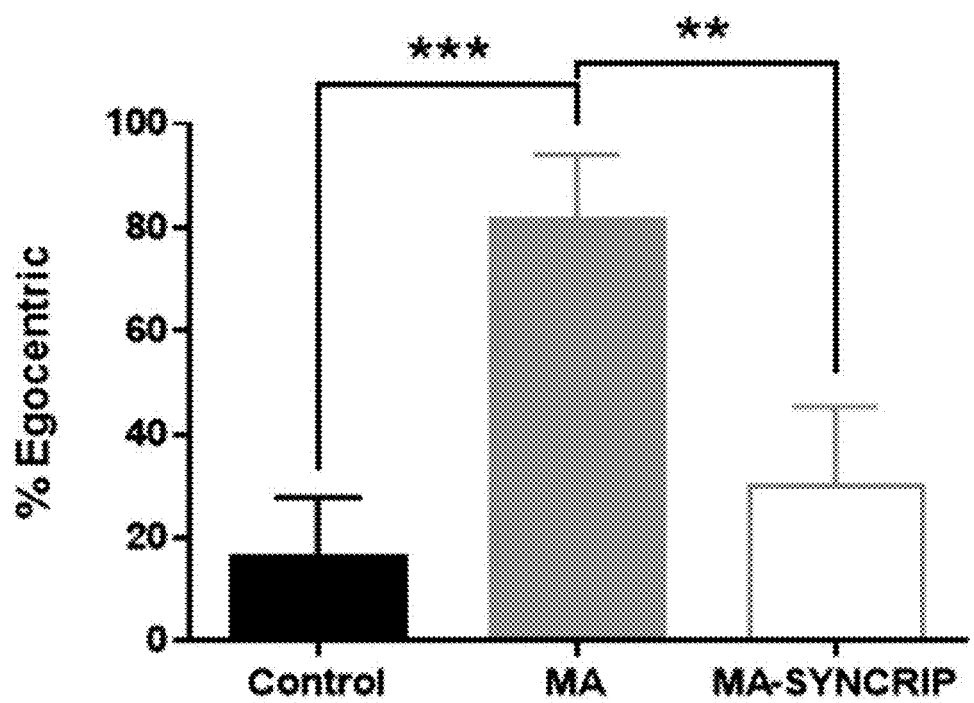
FIG. 12 shows water cross maze test results on a drug addiction animal model (MA), a control group (Control), and an animal model in which SYNCRIP overexpression was induced after drug addiction (MA-SYNCRIP; experimental group)

FIG. 12 shows the water cross maze test results on the drug addiction animal model (MA), the control group (Control), and the animal model in which SYNCRIP overexpression was induced after drug addiction (MA-SYNCRIP; experimental group). As shown in FIG. 12, the egocentric spatial learning of the drug addiction animal model (MA) was abnormally enhanced compared to that of the control group (Control).

In contrast, the spatial learning ability of the animal model in which SYNCRIP overexpression was induced after drug addiction (MA-SYNCRIP) was restored to the level of the control group.

Experimental Example 8. Evaluation of Activity of SYNCRIP Overexpressing Animal Model with Withdrawal Symptoms Caused by Methamphetamine A drug addiction animal model (MA), a control group, and an animal model in which SYNCRIP overexpression was induced after drug addiction (MA-SYNCRIP; experimental group) were prepared in the same manner as in Experimental Example 7. Before methamphetamine injection into each animal model, an open field test was conducted for 20 min to measure the activity of the animal model, which was used as a baseline.

4.0 mg/kg of methamphetamine was administered to the control group (Comparative group 1) and an open field test was again conducted for 20 min to measure the activity of the animal model.

4.0 mg/kg of methamphetamine was administered to the drug addiction animal model (MA) (Comparative group 2) and an open field test was again conducted for 20 min to measure the activity of the animal model.

4.0 mg/kg of methamphetamine was administered to the animal model in which SYNCRIP overexpression was induced after drug addiction (MA-SYNCRIP) (experimental group) and an open field test was again conducted for 20 min to measure the activity of the animal model.

Finally, the activity of each group was compared with the baseline and the activity increase was expressed as a percentage relative to the baseline. The hyperactivities induced by methamphetamine are shown in FIG. 12.

Figure 13:
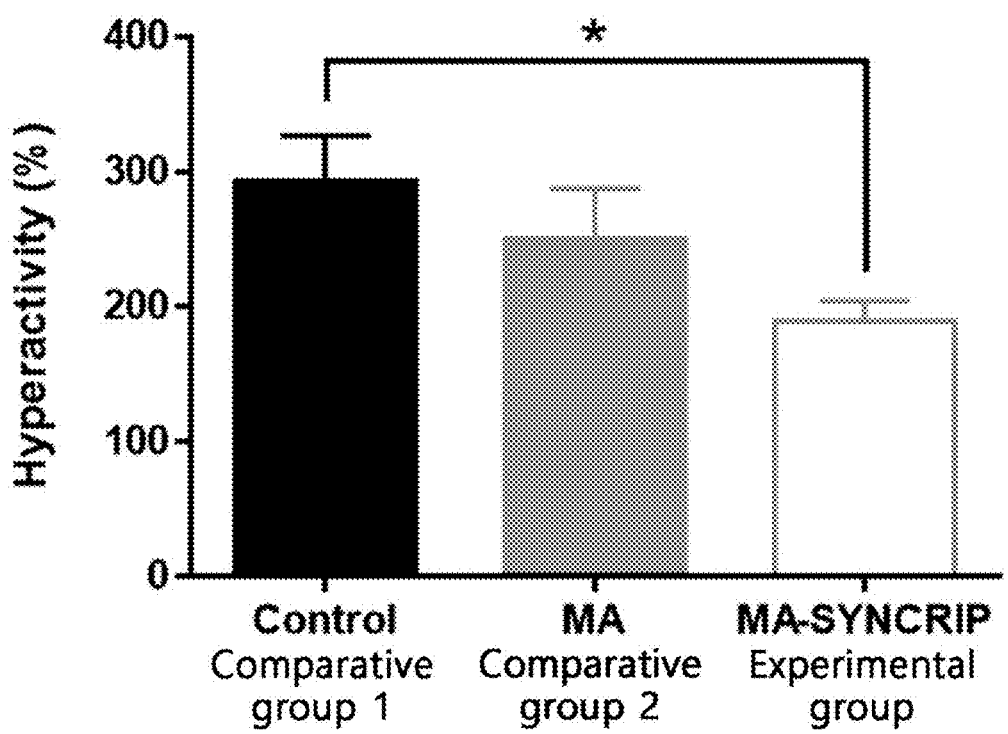
FIG. 13 shows hyperactivities (%) of a drug addiction animal model (MA) and an animal model in which SYNCRIP overexpression was induced after drug addiction (MA-SYNCRIP; experimental group), when methamphetamine was administered.

FIG. 13 shows the hyperactivities (%) of the drug addiction animal model (MA) and the animal model in which SYNCRIP overexpression was induced after drug addiction (MA-SYNCRIP; experimental group), when methamphetamine was administered. As shown in FIG. 13, the methamphetamine injection significantly increased the activities of the control group (Control) and the drug addiction animal model (MA). In contrast, the increase in the activity of the animal model (MA-SYNCRIP) was significantly suppressed despite the administration of methamphetamine. In other words, SYNCRIP was confirmed to have an inhibitory effect on drug dependence even after drug addiction or withdrawal symptoms due to drug addiction occurred.

What is claimed is:

1. A method for screening a therapeutic agent for drug addiction, comprising a) inducing drug addiction in an animal and treating the drug-addicted animal or a biological sample separated therefrom with a candidate agent; b) measuring the synaptotagmin binding cytoplasmic RNA interacting protein (SYNCRIP) gene or its expression level in the candidate agent-treated animal or biological sample, and c) selecting the candidate agent as a therapeutic agent for drug addiction if the measured expression level of the SYNCRIP gene is higher than that in a control group untreated with the candidate agent.

2. The method according to claim 1, wherein the SYNCRIP gene has the sequence set forth in SEQ ID NO: 1.

3. The method according to claim 1, wherein the expression level is measured using a technique selected from the group consisting of polymerase chain reaction (PCR), quantitative polymerase chain reaction (qPCR), reverse transcription polymerase chain reaction (RT-PCR), competitive reverse transcription polymerase chain reaction (competitive RT-PCR), quantitative real-time polymerase chain reaction (qRT-PCR), real-time reverse transcription polymerase chain reaction (real-time RT-PCR), RNase protection assay, Northern blot analysis, and DNA chip analysis.

4. The method according to claim 1, further comprising measuring the expression level of miR-137 in the serum of the candidate agent-treated animal.

5. A method for diagnosing or treating drug addiction, comprising a) measuring the synaptotagmin binding cytoplasmic RNA interacting protein (SYNCRIP) gene or its expression level in a biological sample separated from a subject, b) diagnosing the subject as having drug addiction if the measured expression level of the SYNCRIP gene is higher than that in a normal control group, and c) administering an agent expressing SYNCRIP or promoting the activity of SYNCRIP to the subject diagnosed as having drug addiction.

6. The method according to claim 5, wherein the SYNCRIP gene has the sequence set forth in SEQ ID NO: 1.

7. The method according to claim 5, wherein the expression level is measured using a technique selected from the group consisting of polymerase chain reaction (PCR), quantitative polymerase chain reaction (qPCR), reverse transcription polymerase chain reaction (RT-PCR), competitive reverse transcription polymerase chain reaction (competitive RT-PCR), quantitative real-time polymerase chain reaction (qRT-PCR), real-time reverse transcription polymerase chain reaction (real-time RT-PCR), RNase protection assay, Northern blot analysis, and DNA chip analysis.

* * * * *

SEQUENCE LISTING

```
<160> NUMBER OF SEQ ID NOS: 1

<210> SEQ ID NO 1
<211> LENGTH: 2754
<212> TYPE: DNA
<213> ORGANISM: Artificial Sequence
<220> FEATURE:
<223> OTHER INFORMATION: SYNCRIP

<400> SEQUENCE: 1
actcgcgccg dacacaggga gcagcgagca cgcgtttccc gcaacccgat accatcggac      60
aggatttctc cgcctcagcc caacggggag atctctggaa acatggctac agaacatgtt     120
aatggaaatg gtactgaaga gcccatggat actacttctg cagttatcca ttcagaaaat     180
tttcagacat tgcttgatgc tggtttacca cagaaagttg ctgaaaaact agatgaaatt     240
tacgttgcag ggctagttgc acatagtgat ttagatgaaa gagctattga agctttaaaa     300
gaattcaatg aagacggtgc attggcagtt cttcaacagt ttaaagacag tgatctctct     360
catgttcaga acaaaagtgc cttttttatgt ggagtcatga agacttacag gcagagagaa     420
aaacaaggga ccaaagtagc agattctagt aaaggaccag atgaggcaaa aattaaggca     480
ctcttggaaa gaacaggcta cacacttgat gtgaccactg gacagaggaa gtatggagga     540
ccacctccag attccgttta ttcaggtcag cagccttctg ttggcactga gatatttgtg     600
ggaaagatcc caagagatct atttgaggat gaacttgttc cattatttga gaaagctgga     660
cctatatggg atcttcgtct aatgatggat ccactcactg gtctcaatag aggttatgcg     720
tttgtcactt tttgtacaaa agaagcagct caggaggctg ttaaactgta taataatcat     780
gaaattcgtt ctggaaaaca tattggtgtc tgcatctcag ttgccaacaa taggctttt     840 gtgggctcta ttcctaagag taaaaccaag gaacagattc ttgaagaatt tagcaaagta     900
acagagggtc ttacagacgt cattttatac caccaaccgg atgacaagaa aaaaaacaga     960
ggcttttgct ttcttgaata tgaagatcac aaaacagctg cccaggcaag gcgtaggtta    1020
atgagtggta aagtcaaggt ctgggggaat gttggaactg ttgaatgggc tgatcctata    1080
gaagatcctg atcctgaggt tatggcaaag gtaaaagtgc tgtttgtacg caaccttgcc    1140
aatactgtaa cagaagagat tttagaaaag gcatttagtc agtttgggaa actggaacga    1200
```

```
gtgaagaagt taaaagatta tgcgttcatt cattttgatg agcgagatgg tgctgtcaag    1260
gctatggaag aaatgaatgg caaagacttg gagggagaaa atattgaaat tgtttttgcc    1320
aagccaccag atcagaaaag gaaagaaaga aaagctcaga ggcaagcagc aaaaaatcaa    1380
atgtatgacg attactacta ttatggtcca cctcatatgc cccctccaac aagaggtcga    1440
gggcgtggag gtagaggtgg ttatggatat cctccagatt attatggata tgaagattat    1500
tatgattatt atggttatga ttaccataac tatcgtggtg gatatgaaga tccatactat    1560
ggttatgaag attttcaagt tggagctaga ggaaggggtg gtagaggagc aagggggtgct   1620 gctccatcca gaggtcgtgg ggctgctcct ccccgcggta gagccggtta ttcacagaga    1680
ggaggtcctg gatcagcaag aggcgttcga ggtgcgagag gaggtgccca acaacaaaga    1740
ggccgcgggg tacgtggtgc gaggggtggc cgcggtggaa atgtaggagg aaagcgcaaa    1800
gctgatgggt acaaccagcc agattccaag cggcgccaga ccaataatca gaactggggc    1860
tcccaaccca ttgctcagca accgctccaa ggtggtgatc attctggtaa ctatggttac    1920
aaatctgaaa accaggagtt ttatcaggat acttttgggc aacagtggaa gtagaaacag    1980
tagggcctct gtaaaattgg agactgatag gttgatcaga aactcaccct aaatctgaac    2040
gggtgccgct ataatttgtg acatctggca agatttccct ttatgtatat attttaacaa    2100
tccgcttgga cacgaacaaa gccacacttc taactgcttc tggcgaactg attttatttt    2160
taattttttt caataaagat attcttagat actgaaagaa atagttaatg agtttgcatt    2220
tgtgcttgag aaaatttggc tcaagtccat ttggctgtag tgtcaacgat gtttccagta    2280
gtgtttagat ttggtgtctt caaaggtagt tgattaaaac caagtgtgtc tttaatatct    2340
tgtatcagaa taactttgta tgttaccaac ttaaattgct agaataaggt aaattgatac    2400
acaactgcta tttttaattt agaactttga cctaatttgg gttttcaaaa ccattttggc    2460
tacttgtatt ctttatgctg ttgttttattt caataaaaaa ttcacaccta aatgtatact    2520
tactaaaatt gtgtttacaa ttcgttttc acaaaatttc ctgcaaattt ggttcaaatt     2580
gtatagcatg tcaaggccaa ttaaagggtt ttgtgccttg ttaattcttg tgtggaatat    2640
gtctgcacat tacacaacac tgatttattg cagttttctg cttctggttt aaagtgctat    2700
tttacaacag acttcatgtt cccatcaaaa ataaaaagat aatacatgta gtaa           2754
```